(12) United States Patent
Dybas et al.

(10) Patent No.: US 6,613,558 B1
(45) Date of Patent: *Sep. 2, 2003

(54) METHOD FOR CONVERSION OF A HALOGENATED HYDROCARBON USING A PSEUDOMONAS SP

(75) Inventors: Michael J. Dybas, Lansing, MI (US); Craig S. Criddle, Okemos, MI (US); Gregory M. Tatara, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/474,539

(22) Filed: Jun. 7, 1995

Related U.S. Application Data

(63) Continuation of application No. 08/267,620, filed on Jun. 29, 1994, now abandoned, which is a continuation-in-part of application No. 08/062,072, filed on May 14, 1993, now abandoned.

(51) Int. Cl.⁷ .................................................. B09B 3/00
(52) U.S. Cl. ..................................... 435/262.5; 210/601
(58) Field of Search ........................... 435/262, 262.5, 435/874; 210/601

(56) References Cited

U.S. PATENT DOCUMENTS

| | | | | |
|---|---|---|---|---|
| 4,208,283 A | * | 6/1980 | Brouze | 210/50 |
| 5,024,949 A | * | 6/1991 | Hegeman et al. | 435/262 |

OTHER PUBLICATIONS

Sittig, M., Ed., Handbook of Toxic and Hazardous Chemicals and Carcinogens, 2nd Ed., Noyes Pubs. N.Y. (1985).
Nyer, E.K., Groundwater Treatment Technology, Van Nostrand Reinhold, N.Y. 35–83 (1985).
Criddle et al., Appl. and Environ. Microbiol. vol. 56, No. 11, 3240–3246 (1990).
Kearney, P.C., et al., ACS Symp., 379:352–358 (1988).
Pace, N.R., et al., ASM News, 51:4–12 (1985).
Silver, S. et al., Ed. Pseudomonas: Biotransformations, Pathogenesis and Evolving Biotechnology, ASM Publications, Washington, D.C. Ch. 11,101–120 & Ch.24, 242–267 (1990).
Balch, W.E. and R.S. Wolfe, J. Bacteriol, 137: 264–273 (1979).
Tatara, G.M., et al., Appl. Environ. Microbiol. 59:2126–2131 (1993).
Markwell, M.A., et al., Methods Enzymol. 72:296–301 (1981).
Siegrist, H., et al., Journal of Contaminant Hydrology 2:31–50 (1987).
Stumm, W., et al., Aquatic Chemistry, 2nd ed. John Wiley and Sons, New York, 230–285 (1981).
Lewis, T.A., and R. L. Crawford, Applied and Environmental Microbiology, p. 1635–1641 (1993).
Freeze, R.A., et al., Groundwater, Prentice–Hall Englewood Cliffs, 604 (1979).
Thiem et al., AEM 60, 1059–1067 (1994.
Froment, G.F. and K.B. Bischoff, Chemical Reactor Analysis and Design, 2nd Ed. John Wiley & Sons, pp. 517–537 (1990).
Lewis, Thomas A., et al., Applied and Environmental Microbiology, p. 1635–1641, May 1993.

* cited by examiner

*Primary Examiner*—Curtis E. Sherrer
(74) *Attorney, Agent, or Firm*—Ian C. McLeod

(57) ABSTRACT

A method of remediating an environment containing soil or water contaminated with a halogenated hydrocarbon, particularly carbon tetrachloride, by introducing a Pseudomonas sp. into the environment. In particular, the method converts carbon tetrachloride in the soil or water into carbon dioxide and a non-volatile water soluble fraction, rather than into a toxic chlorinated hydrocarbon with a lesser number of chlorines. Further, pH adjustment in a particular area provides a niche advantage for the Pseudomonas sp in the soil or water for the conversion.

16 Claims, 18 Drawing Sheets

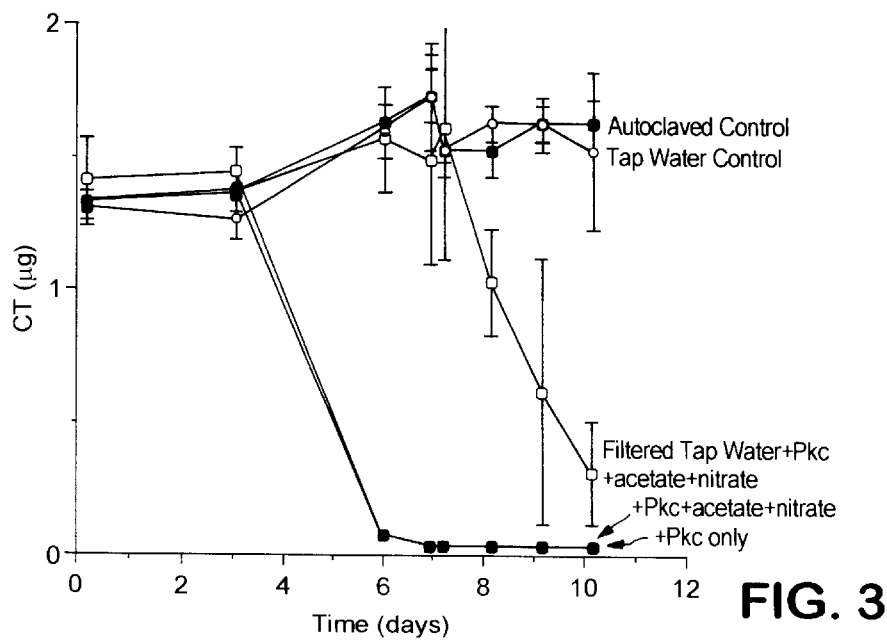
FIG. 3 Transformation of Carbon Tetrachloride in Groundwater by Pseudomonas KC
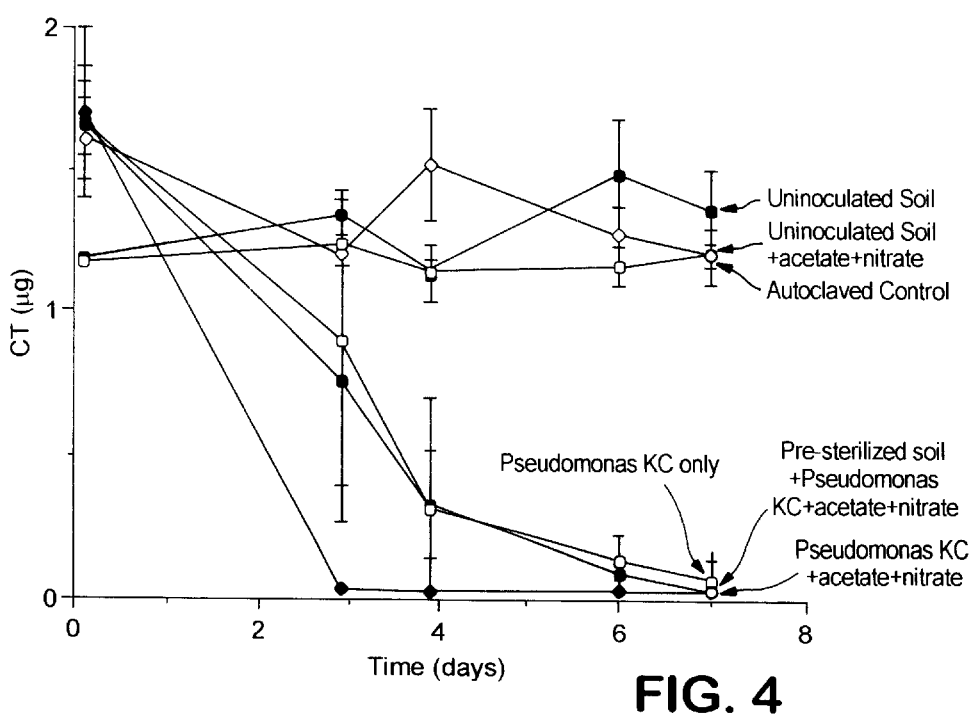
FIG. 4 Transformation of Carbon Tetrachloride in alkaline soil by Pseudomonas KC

METHOD FOR CONVERSION OF A HALOGENATED HYDROCARBON USING A PSEUDOMONAS SP

CROSS-REFERENCE TO RELATED APPLICATION

This is a continuation of application Ser. No. 08/267,620 filed on Jun. 29, 1994 now abandoned which is a continuation in part of application Ser. No. 08/062,072, filed May 14, 1993.

BACKGROUND OF THE INVENTION (1) Field of the Invention

The present invention relates to the use of Pseudomonas sp. for the bioremediation of soil and/or water containing other resident microorganisms and contaminated with halogenated hydrocarbons.

(2) Description of Related Art

In particular, the present invention relates to bioaugmentation of the Pseudomonas sp in situ by the use of pH adjustment to cause suppression of the resident organisms in the soil and/or water so as to convert the halogenated hydrocarbon to carbon dioxide.

Pseudomonas have been well characterized with regard to their ability to dehalogenate various halogenated hydrocarbon compounds in nature. It has been recognized that this activity can potentially be exploited for in situ bioremediation of contaminated groundwater and soil.

Carbon tetrachloride (CT) is presently abundant as contaminant in soil and groundwater and aquifers. Carbon tetrachloride has been proven to pose health and cancer risks (Sittig, M., Ed., Handbook of Toxic and Hazardous Chemicals and Carcinogens, 2nd Ed., Noyes Pubs. N.Y. (1985)). In typical contaminated areas, chloroform is the major breakdown product of carbon tetrachloride. However, chloroform has also been associated with health and cancer risks.

Previous remediation methods utilize extraction of groundwater coupled with above-ground treatment by air stripping or adsorption to activated carbon (Nyer, E. K., Groundwater Treatment Technology, Van Nostrand Reinhold, N.Y., 35–83 (1985)). Air stripping uses large volumes of air to flush and dilute carbon tetrachloride out of water and absorption binds carbon tetrachloride to a solid material. These methods essentially transfer carbon tetrachloride from one media to another without destroying it, thereby leaving the contaminant for disposal.

Pseudomonas sp. strain KC is a denitrifying bacterium that was isolated from aquifer materials collected from Orange County Water District Well #7 of the Naval Weapons Station, Seal Beach, Calif. (Criddle et al., Appl. and Environ. Microbiol. Vol. 56, No. 11, 3240–3246 (1990)). This strain is preferred in the present invention. The publication describes the transformation of CT in sterile laboratory media. The use of the culture in various media in the laboratory is also described in Lewis and Crawford (Lewis, Thomas A. and R. L. Crawford, Applied and Environmental Microbiology, p. 1635–1641 (1993).

A "niche" is a term of art known to ecologists. In the present invention the environment is modified in a way that will often create a niche that can be occupied by a microorganism introduced into the environment and have the strain persist in a way that would otherwise not be possible. The microorganism can then be used to catalyze the degradation of the environmental pollutant.

OBJECTS

It is therefore an object of the present invention to provide a method for conversion of halogenated hydrocarbons in the environment, particularly carbon tetrachloride, into carbon dioxide and water using a Pseudomonas sp. without producing toxic halogenated intermediates in the presence of other microorganisms which are suppressed. It is also an object of the present invention to provide a method wherein a portion of the environment is modified to allow the conversion by the Pseudomonas sp. to take place only in the portion. Further, it is an object of the present invention to provide a method which is simple and economical to perform. These and other objects will become increasingly apparent by reference to the following description and the drawings.

BRIEF DESCRIPTION OF THE DRAWINGS

FIG. 3 is a graph showing transformation of CT in alkaline water. Groundwater (MSU tap water containing 0.051 mg Fe/l) was made alkaline by addition of KOH (pH 8.2). 100 ml samples were dispensed into 120 ml serum vials. The water contained natural microorganisms. The headspace was replaced with nitrogen gas and additions made as indicated. +pkc=inoculated with 1% by volume of Nutrient Broth (Difco, Detroit, Mich.) grown Pseudomonas KC culture. +acetate=300 mg/l sodium acetate, +nitrate=200 mg/l sodium nitrate. Filtered tap water was pre-sterilized using a 0.22 $\mu$m filter. All values represent averages of three independent cultures, and the error bars indicate the standard deviations.

FIG. 4 is a graph showing transformation of CT in soil. 286 g sandy Michigan soil (Metea type soil, B horizon, Michigan State University campus, East Lansing, Mich.) per liter tap water was prepared as a slurry and the pH was raised to 8.2 by addition of KOH. Samples (100 ml) were dispensed into 120 ml serum vials. The soil contained natural microorganisms. Headspace was replaced with nitrogen and additions made as indicated. +Pseudomonas KC=1% inoculum of precipitate free media D grown culture ($5 \times 10^2$ cells/ml initial cell density). +acetate=300 mg/L sodium acetate. +nitrate=200 mg/L sodium nitrate. All values represent averages of three independent cultures, and the error bars indicate the standard deviations.

DETAILED DESCRIPTION OF THE INVENTION

Figure 1:
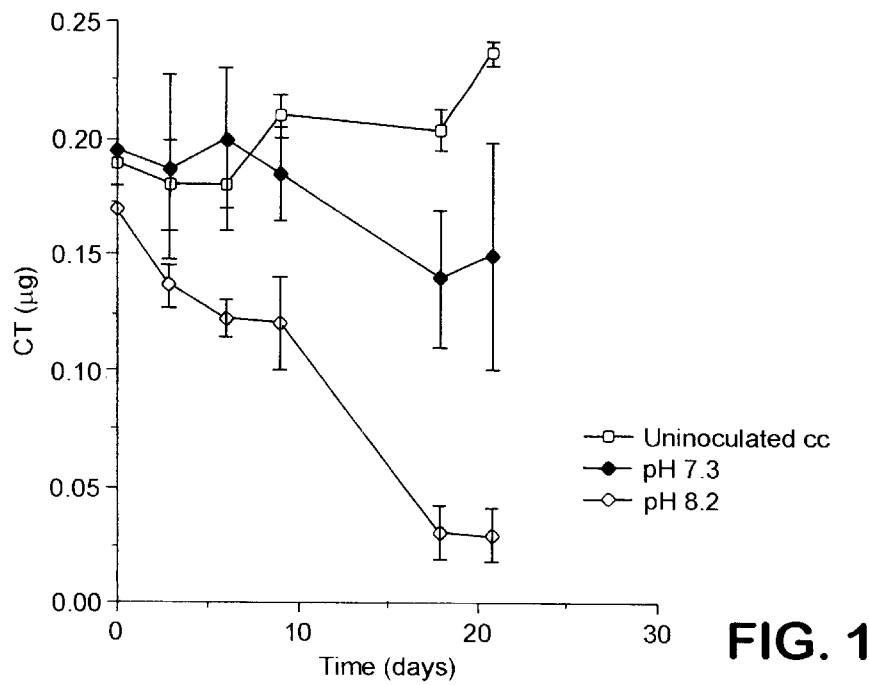
FIG. 1 is a graph showing pH dependence of carbon tetrachloride (CT) transformation in soil. 286 g sandy Michigan soil (Metea type soil, B horizon, Michigan State University campus, East Lansing, Mich.) per liter tap water was prepared as a slurry and the pH was raised to 7.3 or 8.2 by addition of KOH. The soil contained natural microorganisms. Samples (100 ml) were dispensed into 120 ml serum vials. Headspace was replaced with nitrogen. Pseudomonas KC (1% inoculum Nutrient Broth grown culture) was added as indicated. All values represent averages of three independent cultures, and the error bars indicate the standard deviations.

The present invention relates to an improvement in a method of treating soil or water containing a halogenated hydrocarbon and resident bacteria which comprises adjusting the soil or water to an alkaline pH which suppresses metabolism by the resident bacteria in the soil or water; and providing cells of an isolate of a Pseudomonas sp. which acts upon the halogenated hydrocarbon at the alkaline pH in the soil or water so that the halogenated hydrocarbon is converted to carbon dioxide and a non-volatile fraction by the Pseudomonas while the resident bacteria are suppressed.

The present invention relates to a method of treating soil or water contaminated with carbon tetrachloride and containing resident bacteria which comprises:

(a) adjusting the soil or water to an alkaline pH between about 7.8 and 8.2; and (b) providing a concentrate of cells in an isolate of cells of Pseudomonas sp having an ability to degrade $CCl_4$ which is equivalent to Pseudomonas strain PsKC (PsKc) in the soil or water at a level of at least about $10^4$ cells/gm and at a temperature between about 5 and 30° C. so that the carbon tetrachloride is converted to carbon dioxide and a non-volatile fraction by the PsKc while the resident bacteria are constrained.

The present invention particularly provides a method of remediating soil or water in an environment with halogenated hydrocarbon contamination and resident microorganisms by introducing Pseudomonas sp. into the environment, under iron limiting conditions produced by an alkaline pH adjustment and converting the halogenated hydrocarbon directly to carbon dioxide and a non-volatile water soluble fraction. In particular, the present invention provides a niche advantage for the Pseudomonas sp in an environment by adjusting the pH of the environment to about pH 7.8 to 9.2 prior to introducing the Pseudomonas sp. into the environment. The alkaline pH adjustment suppresses the growth of resident bacteria in the soil or water. The present invention describes modifications that can be made to create a suitable niche for the growth of the Pseudomonas sp., particularly PsKC, in an environment.

Bioaugmentation is a potentially useful means for introducing desirable activities into an existing environmental population or ecosystem. By creating a favorable environment or niche for a specific microbe, activities can very often be introduced into an environment by utilizing the microbe as a vector. The activity can be a naturally occurring activity of the microbe or a genetically altered activity. In either case the new or additive activity is introduced into the environment to perform a desired function. For example enzymatic activities expressed by a microorganism in situ have a large number of potential uses, ranging from production of desirable compounds to remediation of unwanted waste compounds. Although the preferred embodiment of the present invention provides a remediant use of the Pseudomonas sp., the present invention further provides means which can be used for the expression of other naturally occurring enzymatic activities or activities occurring as a result of a genetic modification of the Pseudomonas sp.

The halogenated hydrocarbons which can be converted include chlorine, bromine, fluorine, and iodine containing hydrocarbons containing 1 to 8 carbon atoms. Preferred are the one carbon atom compounds containing chlorine and most preferably carbon tetrachloride.

The Pseudomonas sp. can be in the form of a culture in a growth medium in which it is grown, which contains between about $10^4$ and $10^8$ CFU (colony forming units) per gram or ml which is preferred since these cultures contain metabolites which facilitate the conversion. The culture can be concentrated to between about $10^9$ and $10^{12}$ CFU per ml or gram using conventional methods such as centrifugation and or lyophilization. The metabolites can be separately concentrated by freeze-drying and then added to the concentrated culture. Various stabilizers and preservatives well known to those skilled in the art can be included to reduce the death of the cells over time prior to use. In the soil or water the Pseudomonas sp. are preferably present in an amount between $10^3$ and $10^6$ CFU per gram.

The culture medium for the Pseudomonas sp includes a carbon source, a nitrogen source (ammonia, nitrite or amino acids), an electron acceptor (oxygen, nitrate, nitrous oxide and nitrite) and various minerals. Preferably, the medium is low in toxic or inhibitory transition metal ions, particularly iron and copper.

The alkaline pH adjustment suppresses metabolism and colonization by resident bacteria in the soil. Most bacteria are metabolically active at neutral pH's.

The alkaline pH in the soil and water can be produced using any base which does not suppress the Pseudomonas sp. Preferred are alkali metal and alkaline earth metal hydroxides and carbonates are used, such as sodium hydroxide, potassium hydroxide, calcium hydroxide or carbonate. Bases such as ammonium hydroxide can also be used. Organic bases can also be used. Preferably the pH is between 7.8 and 8.2. The conversion by Pseudomonas sp. can be contained to a particular area or niche in the environment by only adjusting the pH.

The present invention particularly provides means for the use of Pseudomonas strain sp. KC (PsKC) for the conversion. More specifically, the present invention utilizes the capability of the PsKC to break down carbon tetrachloride in a contaminated environment in combination with a method of creating an alkaline niche for PsKC such that it can be used in an environment containing diverse microbial populations, such as aquifers, bioreactors, and the like.

PsKC is an aquifer-derived organism that transforms carbon tetrachloride to carbon dioxide and an unidentified non-volatile product without chloroform production under denitrifying conditions (Criddle, Appl. and Environ. Microbiol. Vol., 56, No. 11, 3240–3246 (1990)). PsKC was deposited in the DSM culture collection on Jul. 7, 1992, Deutsche Sammlung von Mikroorganismen Und Zellkulturen GmbH, located at Mascherodor Weg I b, D-3300 Braunschweig, Germany, and is identified by Deposit Number 7136, and was deposited with the American Type Culture Collection (ATCC), 12301 Parklawn Drive, Rockville, Md. 20852 under the Budapest Treaty on Jun. 29, 1994, under Deposit Number ATCC 55595. Other Pseudomonas with the same characteristics can be isolated from the environment.

One aspect of the present invention provides a method of remediating an environment, such as water, soil and the like, in situ as well as in bioreactors, of carbon tetrachloride contamination by the general steps of introducing the PsKC into the affected region of the environment and converting the carbon tetrachloride directly to carbon dioxide and non-volatile water soluble fractions. Critical to the method is the ability of augmenting the environment by an alkaline pH adjustment which allows for the persistence of PsKC and allowing it to perform the remediation function in soils or water wherein the PsKC would not normally be competitive with other microorganisms. This niche advantage is created by adjusting the pH of the affected region of the environment into which the PsKC is introduced to about 7.8 to 8.2 and then introducing the PSKC into the affected region environment. As demonstrated hereinafter, the pH adjustment allows the naturally isolated PsKC microorganism to compete with soil microbial flora and express activities, such as the activity for breaking down the carbon tetrachloride to carbon dioxide, in the presence of indigenous or resident soil microorganisms.

An advantage of the use of the present invention is that it can be used in a transitory manner. The pH of the environment can be adjusted temporarily thereby transiently creating a niche for Pseudomonas sp. PsKC. Once the pH adjustment is either reversed or simply not maintained, the niche ceases to exist. Hence, the PsKC can be preferentially grown in an environment for a purpose of solving an environmental problem and when the problem is solved, the niche can be removed.

Generally, the protocol includes the steps of initially adjusting the pH of an environment such as an aquifer or groundwater to the preferred pH range of 7.8 to 8.2. The culture of PsKC are pumped or injected into the aquifer or groundwater source and supplemented with required growth factors including electron donors, such as acetate or glycerol; electron acceptors, such as nitrate and other nutrients if any are limiting at the site. These growth limiting factors are supplied by various means including alternate pulsing of growth factors at a single well, addition of separate growth factors in separate wells with downstream mixing; or direct introduction of all required growth factors at a single well.

Finally, the dispersion of the bacteria and expression of the activity of the bacteria is monitored by means well known in the art.

More specifically, the following protocol is used:

Niche Adjustment

Prior to addition of Pseudomonas sp (PSKC) the pH of the water or soil is adjusted to pH 7.8–8.2 by addition of KOH or NaOH or other alkaline materials which are non-toxic to the Pseudomonas sp. Direct injection or pump controlled injection of aqueous base solution in combination with pH measurements of the soil or groundwater extracted from the environment is used to control and monitor the pH. Nutrients are added by direct injection or pump controlled injection and are measured by laboratory practices standard in the arts. For example, acetate and phosphate are measured by ion chromatographic analysis of extracted groundwater samples.

Growth and Inoculation/Pseudomonas sp. (PsKC) Addition

Cultures of Pseudomonas sp. (PsKC) are grown preferably under aerobic conditions or denitrifying conditions to a level of about $10^6$ to $10^{11}$ CFU per gram or ml. The growth media used contains a carbon source, a nitrogen source, minerals and a source of oxygen (oxygen or a nitrate for instance) and minerals which facilitate growth. The cells can be used directly or concentrated by various means, such as centrifugation and/or lyophilization. Cells were added to a reasonable concentration of about $10^5$ to $10^6$ cells per gram by direct injection or pump controlled injection to samples containing carbon tetrachloride under denitrifying conditions.

Analytical

Carbon tetrachloride levels are followed by headspace gas chromatography.

Monitoring of Bacterial Movement

An enumeration/screening method based on colony morphology and a siderophore or other metabolite production can be used to follow the bacteria. Several methodologies known in the arts such as BIOLOG and probe technologies (Kearney, P. C., et al., ACS Symp., 379:352–358 (1988); and Pace N. R., et al., ASM News, 51:4–12 (1985)) are used to enhance detection and monitoring bacteria movement.

Another aspect of the present invention recognizes that the method of augmenting the growth of the Pseudomonas sp (PsKC) such as in an environment, such as water and soil sources including aquifers, bioreactors, and the like, can be utilized to introduce the PsKC to bioaugment an environment with desirable activities outside the scope of remediation. That is, other activities, such as other enzymatic activities and non-enzymatic (e.g. siderophores, extracellular polysaccharides, cofactors, etc.) which may or may not be related to bioremediation can be expressed by genetically altered strains of the Pseudomonas sp. for various potential uses, ranging from the production of desirable compounds to remediation of unwanted waste compounds in a manner which potentiates the method described above. Alternatively, the introduction of the Pseudomonas sp. to environments that have been modified to provide a niche for Pseudomonas sp. can allow delivery of native activities of the Pseudomonas sp. to the environment. For example, unaltered Pseudomonas sp. can be used as a vector to provide activities such as toluene degradation and dichloromethane degradation, as well as other naturally occurring activities into an environment.

The present invention provides a method of augmenting growth of the Pseudomonas sp. such as in an environment by adjusting the pH of the environment or region of the environment to about 7.8 to 8.2 prior to introducing the Pseudomonas sp. into the environment. The Pseudomonas sp. can be a genetically modified strain having a specific activity introduced into the Pseudomonas sp. by genetic modification thereby bioaugmenting the source with a specific activity by introducing the genetically modified strain of the Pseudomonas sp. into the source. For example, the Pseudomonas sp. can have an increased activity of a specific enzyme. As the present invention provides means for allowing the Pseudomonas sp. to survive in the environment in competition with the indigenous microorganisms and other factors therein, the added desirable activity of the genetically modified Pseudomonas sp. can be expressed in the environment. In other words, the present invention allows the Pseudomonas sp. to act as a vector for delivering genetically engineered activities into an environment. As stated above, the Pseudomonas sp. can also introduce activities of non-genetically modified strain into the environment.

The Pseudomonas sp. can be modified by various means well known in the art (Silver, S. et al., Ed. Pseudomonas: Biotransformations, Pathogenesis and Evolving Biotechnology. ASM Publications, Washington, D.C., Ch.11, 101–120, Ch. 24, 242–267 (1990)).

The present invention can be utilized as a delivery mechanism for an indigenous activity possessed by the Pseudomonas sp. or as a vector for delivering the genetically engineered activities as discussed above. In practice, this can be accomplished by adjusting the pH of the aquifer, groundwater, soil, or other environment such as a bioreactor to the pH of 7.8 to 8.2. The Pseudomonas sp. can be pumped or injected as a culture into the environment, the Pseudomonas sp. having the desired genotype/phenotype. As discussed above, growth factors and nutrients can be supplemented into the environment if any are limiting at the site. Finally, the dispersion of the Pseudomonas sp. and expression of the activity are monitored.

The preferred method of enumerating and monitoring the persistence of the Pseudomonas sp. obtained from the various sources discussed above while transforming carbon tetrachloride to carbon dioxide generally includes the steps of obtaining a sample from the source which need be monitored, inoculating the sample onto minimal media plates using acetate as a sole carbon source, and screening the unique morphology and siderophore iron binding activity of the Pseudomonas sp. on siderophore assay agar plates.

In addition to culture based detection methods, molecular tracking methods can be developed by those skilled in the arts (Thiem et al., AEM, 60 1059–1067 (1994); Pace, N. R., et al., Analyzing Natural Microbial Populations by rRNA sequence. ASM News 51:4–12 (1985)).

The above aspects of the present invention can be utilized in combination so as to provide means for remediating contaminated water and soil sources or other environments of carbon tetrachloride utilizing indigenous activities of the Pseudomonas sp. or genetically altered Pseudomonas sp. for either remediation purposes or other purposes.

The following Examples 1 to 5 demonstrate the kinetics of carbon tetrachloride transformation by PsKC, and accelerated carbon tetrachloride transformation obtained in iron-rich groundwaters and soil slurries by adding the PsKC after the pH adjustment in accordance with the present invention to thereby augment the growth of the PsKC.

Chemicals Carbon tetrachloride (CT, 99% purity) was obtained from Aldrich Chemical Co., Milwaukee, Wis. All chemicals for media preparation were ACS reagent grade (Aldrich or Sigma Chemical Co.), and all water used was 18 megohm resistance or greater and was thus substantially free of salts.

Media Preparation and Growth Conditions

Medium D [3] contained (per liter of deionized water) 2.0 g of $KH_2PO_4$, 3.5 g of $K_2HPO_{41}$ 1.0 g of $(NH_4)2SO_4$, 0.5 g of $MgSO_4 \cdot 7H_2O$, 1 milliliter of trace nutrient stock TN2, 1 milliliter of 0.15 M $Ca(NO_3)_2$, 3.0 g of sodium acetate, and 2.0 g of sodium nitrate. Medium D was prepared with trace nutrient stock solution TN2. Stock solution TN2 container (per liter of deionized water) 1.36 g of $FeSO_4 \cdot 7H_2O$, 0.24 g of $Na_2MoO_4 \cdot 2H_2O$, 0.25 g of $CUSO_4 \cdot 5H_2O$, 0.58 g of $ZnSO_4 \cdot 7H_2O$, 0.29 g of $Co(NO_3)_2 \cdot 6H_2O$, 0.11 g of $NiSO_4 \cdot 6H2O$, 35 mg of $Na_2SeO_3$, 62 mg of $H_3BO3$, 0.12g of $NH_4VO_3$, 1.01 g of $MnSO_4 \cdot H_2O$, and 1 ml of $H_2SO_4$ (concentrated). Some experiments used different trace metal preparations to study their effects on CT transformation. TN2-Cu (or minus Cu) and TN2-Fe (or minus Fe) stock solutions lacked $CuSO_4 \cdot 5H_2O$ and $FeSO_4 \cdot 7H_2O$, respectively, but were otherwise identical to $TN_2$. After addition of all essential media components, medium D was adjusted to a desired initial pH of 8.0 or 8.2 with 3N KOH. This final adjustment in pH resulted in the formation of a white precipitate. The resulting medium was autoclaved at 121° C. for 30 minutes and transferred to an anaerobic glove box for degassing.

Precipitate-free medium D was prepared as follows: medium D (adjusted to an initial pH of 8.0 or 8.2) was autoclaved at 121° C. for 30 minutes, transferred to an anaerobic glove box for degassing and quiescent settling of precipitate, and decanted after 24 hours. The precipitate-free and oxygen-free decanted medium was re-autoclaved for 30 minutes at 121° C. and cooled before use. Precipitate-free medium D contained 24 mM acetate, 25 mM PO4 3, 19mM $NO_3$, and 3.8 nM iron, as determined by atomic absorption spectroscopy and ion chromatography.

Cultures were grown under a $N_2$ atmosphere in one of three different containers (1) 28 mL serum tubes (Bellco Glass NO. 2048–00150, Vineland, N.J.), a modified one-liter Wheaton Bottle as described by Balch and Wolfe (Balch, W. E. and R. S. Wolfe, J. Bacteriol. 137: 264–273 (1979)), and (3) 250 mL (8oz.) bottles sealed with screw-cap Mininert valves (Alltech, Deerfield, Ill., catalog number 95326). Both the serum tubes and the modified Wheaton bottles were sealed with Teflon®-faced butyl rubber septa (West Company, Lititz, Pa., Catalog number 1014–4852) and aluminum crimp seals. All cultures were shaken at 100–150 rpm at 20–23° C. PsKC did not transform carbon tetrachloride at temperatures above 25° C., and it did not grow at temperatures above 30° C. (data not shown). The culture had the characteristics shown in Table 1, Effects of Trace Metals To assess the effect of trace copper, medium D was prepared with either stock solution TN2 or TN2-Cu, transferred to 8-oz (250 mL) bottles, sealed, autoclaved, cooled

TABLE 1

Characteristics of Pseudomonas sp. strain KC and *P. stutzeri*[a]

| Organism | Cell length ($\mu$m) | Cell diam ($\mu$m) | Nitrate reductase | Phenylalanine | Citrate | Urea | Lysine | Arginine | Ornithine | Sucrose | Malonate | Anaerobic glucose | Adonitol |
|---|---|---|---|---|---|---|---|---|---|---|---|---|---|
| Pseudomonas strain KC | 1.2–2.1 | 0.4–0.6 | + | — | + | — | — | — | — | — | + | — | — |
| P. stutzeri | 1.4–2.8 | 0.7–0.8 | + | d | + | NI | — | — | — | — | d | — | — |

| Organism | Aerobic glucose | Maltose | Arabinose | Inositol | Raffinose | Sorbitol | Lactose | Rhamnose | Growth with nitrite | Oxidase | Xylose | Glycerol |
|---|---|---|---|---|---|---|---|---|---|---|---|---|
| Pseudomonas strain KC | +[a] | — | — | — | — | —[b] | — | — | +[c] | + | — | + |
| P. stutzeri | + | + | — | — | NI | — | — | — | + | + | — | + |

[a]From Bergey's Manual of Systematic Bacteriology (12). d, 11 to 89% of strains are positive; NI, not indicated.
[b]+ after 48 hs.
[c]Gas evolution observed.

and was generally similar to P. stutzeri, which did not degrade CT in the manner of PsKC. Culture manipulations were typically performed in a Coy anaerobic glove box (Coy Laboratories, Ann Arbor, Mich.) under an atmosphere of 98% $N_2$ and 2% $H_2$. Oxygen level was monitored continuously with a Coy gas detector model number 10. Hungate technique utilizing $N_2$ flushing was used for anaerobic manipulations outside the glove box.

Analytical Methods

All bottles used to evaluate carbon tetrachloride transformation were sealed with pressure tested screw-cap Mininert valves or TEFLON-lined butyl rubber stoppers. Carbon tetrachloride was assayed by removing 0.1 mL of headspace gas with a 0.25 or 0.5 mL precision gas-tight syringe (Alltech catalog number 050032), closing the syringe valve, inserting the syringe needle through the injection port septum, opening the syringe valve, and injecting the sample into the GC. For ppb concentrations, the GC was a Perkin Elmer model 8500 equipped with a 100/120 mesh column (10% Alltech CS-10 on a Chromsorb W-AW, Alltech catalog number 12009 PC) and an electron capture detector with nitrogen carrier (40 mL/min) and nitrogen make-up (27 mL/min). For ppm concentrations, the GC was a Hewlett Packard 5890 gas chromatograph operated isothermally at 150° C. and equipped with a DG 624 column (J&W Scientific, Folsom, Calif. catalog number 125–1334) and a flame ionization detector (hydrogen flowrate=100 mL/min, air flowrate=250 mL/min). The carrier gas was nitrogen (16 mL/min).

External standard calibration curves were prepared by addition of a primary standard (7.8 ng carbon tetrachloride pr $\mu$g carbon tetrachloride pr $\mu$L methanol) to secondary standard water solutions having the same gas/water ratio, ionic strength, incubation temperature, and speed of shaking as the assay sample. A four point calibration curve was prepared over a concentration range bracketing that of the assay samples. Protein was stored by freezing at −20° C., and assayed using the modified Lowry method, with bovine serum albumin as the standard (Markwell et al, Methods in Enzymology 72 296–303 (1981)).

and inoculated with a 1% by volume inoculum of a stationary phase culture of Pseudomonas KC (about $10^8$ to $10^9$ CFU/gram). Cultures were grown to stationary phase, spiked with carbon tetrachloride, and assayed for carbon tetrachloride transformation.

To assess the effects of trace iron, medium D and precipitate-free medium D were prepared using trace metal stock solutions TN2 and TN2-Fe. Cultures were grown 48 or 72 hours, spiked with carbon tetrachloride, and assayed for carbon tetrachloride transformation. To assess iron inhibition, 10 mL of early stationary phase culture (grown for 72 hours in precipitate-free medium D) was transferred to 28 mL serum tubes in an anaerobic glove box, spiked with 0–20 $\mu$M ferric iron (as ferric ammonium sulfate), and equilibrated for 10 minutes. The serum tubes were sealed with TEFLON-lined rubber stoppers, spiked with carbon tetrachloride, shaken throughout the experiment on a shaker table, and monitored by sampling of the gas phase.

Transformation in Groundwater and Soil Systems

The groundwater used in bioaugmentation experiments was Michigan State University, East Lansing, Mich. tap water. After adjusting the pH of the groundwater to 8.2 with 3N KOH, unsterilized groundwater or filter-sterilized (0.22 $\mu$ filter) groundwater was dispensed into a suite of autoclaved 120 mL serum bottles. Some bottles serve as uninoculated controls for abiotic losses. The remainder were inoculated with 1% by volume inoculum of strain KC grown on 1% Nutrient Broth (Difco Co.) (about $10^8$ to $10^9$ CFU/gram. Some of the inoculated bottles were autoclaved, while others received additions of acetate (300 mg/L as sodium acetate) and nitrate (200 mg/L as sodium nitrate). The headspace above all samples was replaced with nitrogen, but no effort was made to remove oxygen dissolved in the water. All bottles were sealed with TEFLON-lined rubber stoppers, spiked with 1.5 $\mu$g carbon tetrachloride, placed on a shaker table, and monitored by sampling of the gas phase.

Soil slurry experiments were conducted using Metea type soil from the B horizon at Michigan State University, East Lansing, Mich. (0.7% organic matter, 31 ppm iron, 4.8 ppm nitrate and 9.9 ppm ammonia). Soil slurries (286 g in 100 mL tap water) adjusted to pH 8.2 with 3N KOH were dispensed into 120 mL serum vials. Some samples were sealed and autoclaved to serve as abiotic controls for sorption and volatilization losses. Controls for the possible transformation of carbon tetrachloride by indigenous microflora were prepared by sealing serum bottles with or without the addition of acetate (300 mg/L as sodium acetate) and nitrate (200 mg/L as sodium nitrate). The remaining bottles received a 1% inoculum of strain KC (grown on precipitate-free medium D) giving an initial cell density of $5 \times 10^2$ cells/mL. Some of the inoculated bottles were amended with acetate (300 mg/L as sodium acetate) and nitrate (200 mg/L as sodium nitrate). The headspace above all samples was replaced with nitrogen, but no effort was made to remove dissolved oxygen. All samples were sealed with TEFLON-lined rubber stoppers, spiked with 1.5 μg carbon tetrachloride, placed on a shaker table, and monitored by sampling of the gas phase.

EXAMPLE 1

FIG. 1 and Table 2 show the effect of pH on growth yield of PsKC and on carbon tetrachloride transformation by PsKC in soil.

Table 2 shows the pH dependence of growth yield of PsKC. Precipitate free Media D was prepared at various pH and inoculated with 1% by volume of a 72 hour grown PsKC culture. Protein was determined after 72 hours growth by the method of Lowry. CFU/gram was determined by calculating from measurement of the number of cells per milligram protein. All values are averages of duplicate cultures. There are about $1.72 \times 10^{-7}$ micrograms of protein per cell.

TABLE 2 pH dependence of growth yield of Pseudomonas KC

| pH growth media | Yield (CFU/gm) (μg protein/ml) | |
|---|---|---|
| 7.4 | $1.9 \times 10^7$, | 3.3 |
| 7.8 | $3.6 \times 10^7$, | 6.3 |
| 8.0 | $6.5 \times 10^7$, | 11.3 |
| 8.2 | $8.1 \times 10^7$, | 14.0 |
| 8.5 | $8.3 \times 10^7$, | 14.3 |
| 9.0 | $1.2 \times 10^8$, | 21.2 |
| 10.0 | 0 | 0 |

Growth yield increased between pH 7.8 and 9.0. The cells grew until about pH 9.6. Also, a concomitant significant difference in carbon tetrachloride transformation occurred between 7.3 and 8.2.

Table 3 shows the transformation of CT by PsKC which was first order for cell protein and first order with respect to substrate concentration (Tatara et al, Applied & Environmental Microbiology 59, 2126–2131 (1993) published by the inventors herein). Pseudo second order rate constants were determined for transformation of CT by cultures grown in various media. All values represent the averages of three independent cultures showing standard deviations.

TABLE 3

Pseudo-Second Order Rate Coefficients for Co-Metabolism of Carbon Tetrachloride

| Media | Growth time (hrs) | k' (L/mg protein/day) |
|---|---|---|
| Media D | 48 | 0.893 +/− 0.03 |
| | 72 | 0.362 +/− 0.08 |
| Precipitate free Media D | 48 | 6.18 +/− 0.48 |
| | 72 | 2.28 +/− 0.45 |
| Media D-Fe | 48 | 3.93 +/− 1.48 |
| | 72 | 4.03 +/− 0.79 |
| Precipitate free Media D-Fe | 48 | 9.07 +/− 1.24 |
| | 72 | 4.41 +/− 0.56 |

Figure 2:
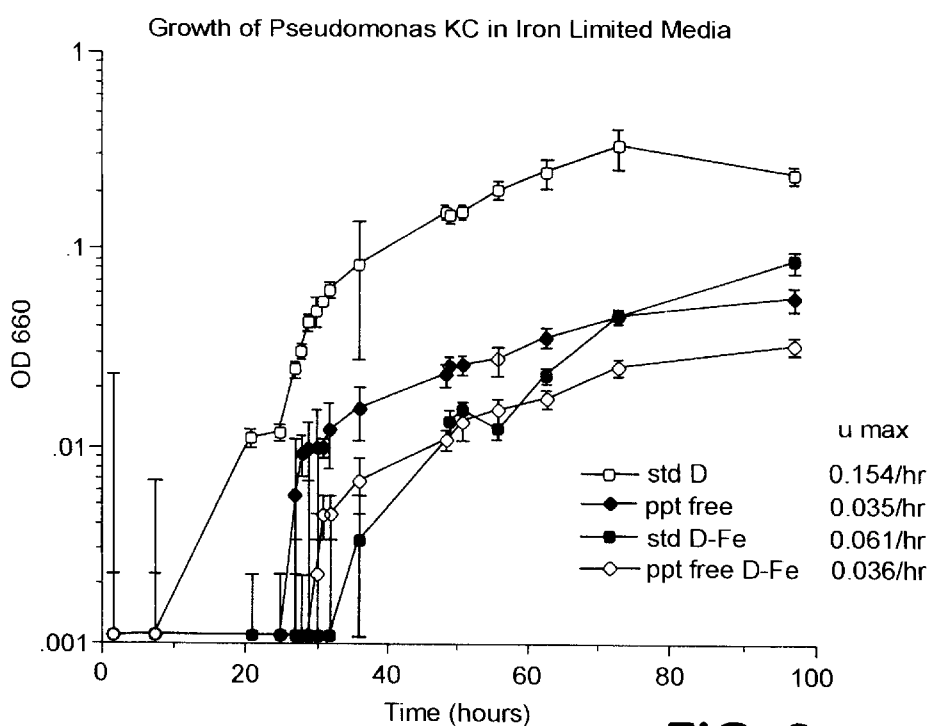
FIG. 2 is a graph showing growth of Pseudomonas KC in medium D with and without modification (iron and/or precipitate free). All values represent averages of triplicate cultures, and error bars indicate the standard deviations.

As shown in Table 3, pseudo-second order rate coefficients k' for carbon tetrachloride transformation (units of liter per milligram protein per day) generally decreased as cultures aged from 48 to 72 hours, indicating decay of transformation activity as cells entered the stationary phase. The exception was cultures grown in medium D with TN2-Fe. These cultures continued to grow between 48 and 72 hours, and showed no decrease in the second order rate coefficient over this period. Growth rates for these cultures were higher and less variable than those of cultures grown in precipitate-free media (FIG. 2). These observations suggest that, for this medium, cell growth and production of carbon tetrachloride transformation activity may be controlled by the solubilization of iron in the precipitate.

EXAMPLES 2, 3 and 4

Examples 2, 3 and 4 show the transformation in groundwater and soil systems.

Figure 5:
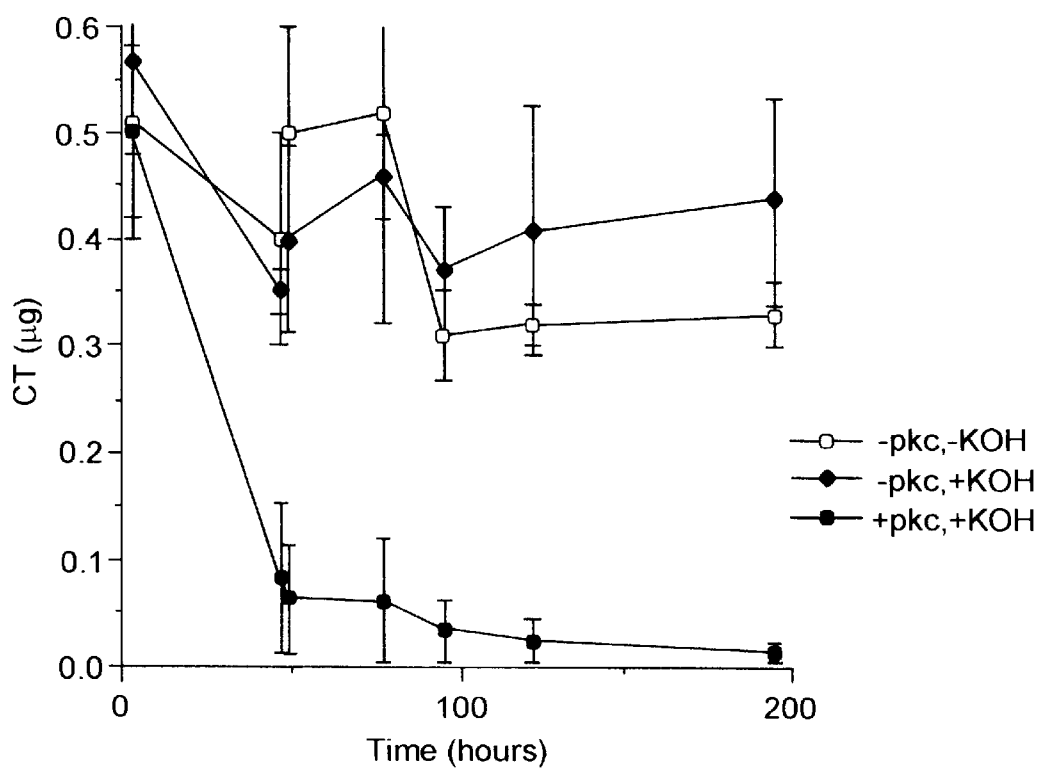
FIG. 5 is a graph showing transformation of CT in groundwater from a CT contaminated aquifer in Schoolcraft, Mich. The water contained natural microorganisms. 10 ml samples of groundwater were dispensed in Balch tubes under nitrogen. pH was adjusted to 8.2 as indicated by +KOH, and Pseudomonas KC (1% inoculum, nutrient broth o/n culture) added as indicated by +pkc. Values represent averages of three independent cultures, and the error bars indicate the standard deviations.

As shown in FIGS. 3, 4 and 5, inoculation of groundwater or soil slurries (pH adjusted to 8.2) with Pseudomonas sp. strain KC increased the rate of carbon tetrachloride transformation. Carbon tetrachloride did not disappear in pH-adjusted controls that were not inoculated with strain PsKC. Addition of strain PsKC by itself was a sufficient condition for carbon tetrachloride transformation. Acetate and/or nitrate additions were not required.

The above results demonstrate the functionality and utility of the present invention with regard to converting carbon tetrachloride in a remediating situation directly to carbon dioxide and a non-volatile water soluble fraction. The data further demonstrate the criticality of the pH of the medium for the activity of the break-down of the carbon tetrachloride by the PsKC as well as the criticality of the pH vis-a-vis the persistence of the PsKC strain.

EXAMPLE 5

The addition of alkali to create the iron-limited conditions was used for CT transformation to provide a competitive advantage for strain PsKC in non-sterile environments. By supplying acetate and adjusting pH to 7.9–8.2, growth of strain PsKC was enhanced, and CT degradation was observed in non-sterile soils, model aquifer materials, and groundwater. Columns operated under non-sterile conditions were used to evaluate the effects of alkali niche adjustment on strain PsKC transport, colonization, and CT degradation. In these systems, strain PsKC was transported with or ahead of a bromide tracer. In a continuous flow column, a region of colonization was obtained, and a sustained removal of 20–30 ppb CT was observed. Colonization and CT removal were also observed in batch exchange columns operated under non-sterile conditions.

MATERIALS AND METHODS

Chemicals. Tetrachloromethane (CT, 99% purity) was obtained from Aldrich Chemical Co., Milwaukee, Wis. Ottawa sand was obtained from Soiltest, Inc. of Lake Bluff, Ill. All chemicals used were ACS reagent grade (Aldrich or Sigma Chemical Co.). All water used in reagent preparation was deionized 18 Mohm resistance or greater.

Media. Medium D was prepared and dispensed in 28 mL serum tubes or modified 1-liter Wheaton bottles as previously described. Nutrient broth and nutrient agar (Difco) plates were prepared according to manufacturer's instructions. Cultures were grown at 20° C. with 150 rpm shaking under aerobic or denitrifying ($N_2$ headspace) conditions to a level of about $10^7$ to $10^{11}$ CFU per gm or ml, depending upon the growth conditions. High iron produces a high yield and low induction. Low iron produces a lower yield but the most active cells. The conditions can be aerobic or anaerobic. The dependence of growth of strain PsKC and the Schoolcraft aquifer native microbial flora as a function of initial medium pH was determined by preparing medium D at various initial pH levels (modified by addition of nitric acid or NaOH). Ten milliliter aliquots of media D at pH 7–10 were inoculated with a 1% inoculum of nutrient broth grown strain PsKC or aquifer microbial flora, and growth was followed by protein levels.

Analytical Methods. CT was assayed by removing samples of headspace gas above liquid samples and detected by gas chromatography as described previously (Tatara, G. M., et al., Appl. Environ. Microbiol. 59:2126–2131 (1993); the inventors herein). External calibration standards were prepared by addition of a primary CT standard in methanol to generate a 4 point calibration curve which bracketed the concentrations in the assay samples (Tatara, G. M., et al., Appl. Environ. Microbiol. 59:2126–2131 (1993)).

Bromide, acetate, phosphate and other ions were assayed by ion chromatography (Dionex model 2000i/SP ion chromatograph with suppressed conductivity detection equipped with a Sarsep AN 300 anion exchange column and utilizing a 1.8 mM bicarbonate/1.7 mM carbonate mobile phase at 1 ml/min). Chromatograms were recorded and data integrated using a Spectra Physics model SP 4270 integrator. External standard calibration curves were prepared by diluting primary ion standards into secondary water standards having the same ionic composition as the test samples.

Measurements of pH were made with an Orion model 720A pH meter. Protein was determined by the modified Lowry method, with bovine serum albumin as the standard (Markwell, M. A., et al., Methods Enzymol. 72:296–301 (1981)).

Groundwater. Groundwater from a CT-contaminated aquifer in Schoolcraft, Mich., was used in all batch and column studies. Groundwater samples were obtained manually by withdrawing groundwater from a 2"steel well screened at 30 feet below the water table with a TEFLON bailer. Groundwater samples were stored in pre-sterilized sealed NALGENE carboys or in Wheaton bottles equipped with TEFLON lined caps at 4° C.

CT transformation in groundwater samples. Ten milliliter samples of Schoolcraft aquifer groundwater were dispensed in 28 mL balch tubes under nitrogen and sealed with TEFLON lined stoppers. The pH of the groundwater was adjusted by addition of 3N KOH or NaOH to pH 8.2, and strain KC was added (1% by volume (about $10^8$ CFU/gram) inoculum from an 18 hour nutrient broth grown culture). Uninoculated and unadjusted samples served as controls. Samples were shaken at 150 rpm and incubated at 20° C. Headspace gas samples (0.1 mL) were periodically removed for CT analysis.

CT transformation in soil samples. Slurries of Metea B horizon soil (5% wt/wt) were prepared as previously described (Tatara, G. M., et al., Appl. Environ. Microbiol. 59:2126–2131 (1993)), and pH was adjusted by addition of 3 M KOH. Samples were then inoculated with strain PsKC (1% inoculum from an 18 hour nutrient broth grown culture). Uninoculated and pH-unadjusted samples served as controls. Samples were shaken at 150 rpm and incubated at 20° C. Headspace gas samples (0.1 mL) were periodically removed for CT analysis.

Enumeration of Pseudomonas sp. strain KC. To determine the extent of colonization by strain KC in model aquifer systems, the concentration of cells and protein were determined in extracted groundwater samples. Samples of groundwater were aseptically extracted from the model aquifer or collected during exchange events. Protein levels were determined by the Lowry method. Serial dilutions of the extracted samples were performed in medium D or in sterile phosphate buffer (2 mM, pH 8.0). Diluted aliquots (100 ul) were spread on nutrient agar plates. Total cell numbers and initial estimates of strain PSKC levels were determined by counting colonies after 6 days of incubation at 20° C. When grown on nutrient agar plates, a "fried egg" colony morphology characteristic of strain KC is observed. Quantification was also obtained by serial dilutions in medium D containing 7 ug/L CT. Tubes were incubated 6 days at 20° C. Growth was determined by optical density, and CT and CF levels were assayed by GC. A dilution tube which showed growth and degraded >3 ug/L CT without detectable CF production was scored as positive for the presence of strain PsKC. Indigenous organisms did not degrade CT. organism concentrations on the solids (biofilm) were not determined to avoid disruption of the solid matrix.

Pseudomonas sp. strain PsKC persistence in pH adjusted groundwater. To determine the effect of pH on the persistence of Pseudomonas sp. strain PsKC, groundwater was pasteurized (65° C., 8 hours) to kill native microbial flora without generation of the precipitate formed during autoclaving of the groundwater. To this pasteurized groundwater, a sterile 100 mM sodium carbonate solution and sterile $CO_2$ gas were added to adjust the pH to 8.2. Three replicate experiments were performed by adding $2 \times 10^6 - 1 \times 10^7$ Pseudomonas sp. strain KC cells/ml without a carbon source or electron acceptor. Aliquots were removed at 1–4 day intervals and levels of Pseudomonas sp. strain KC were determined by serial dilution and plate counts as described above. After 14 days, the pH was adjusted to pH 7.5 by addition of $CO_2$ gas, and levels of Pseudomonas sp. strain KC were followed for an additional 7 days.

Batch exchange column studies. Batch exchange columns studies were conducted using a modification of the method of Siegrist and McCarty (Siegrist, H., et al., Journal of Contaminant Hydrology 2:31–50 (1987)) to evaluate cell transport, and to determine whether strain KC could persist and degrade CT under non-sterile operating conditions. A Harvard syringe pump operated at a flowrate of 2.5 mL/min was used to rapidly exchange the liquid contents of a column packed with either sand, glass beads, or aquifer material. During an exchange, the displaced pore fluid was collected in 28 mL Balch tubes sealed with TEFLON-lined septa. To prevent pressurization of the tube during sample collection, 5 mL of air was removed from the sealed Balch tubes immediately prior to sampling. A 5 mL sample of pore fluid was then collected by passage through a needle into the Balch tubes. CT, bromide, acetate, phosphate, protein, optical density and cell number were determined in these samples. Samples were assayed immediately following exchanges when possible. All samples were stored at 4° C. and assayed within 24 hours.

Batch exchange column studies using glass beads and sand. Initial evaluation of strain PsKC transport under aerobic and denitrifying conditions and CT transformation under denitrifying conditions was performed using KONTES, Vineland, N.J. glass columns (30×1 cm) equipped with TEFLON stopcock, fittings and 1/16" TEFLON tubing and packed with autoclaved Ottawa sand or glass beads (5 mm diameter). Aerobic and anaerobic columns were prepared with Ottawa sand. All columns were prepared aseptically in a laminar flow germ free hood except the anaerobic Ottawa sand columns which were prepared aseptically in a Coy anaerobic glove box containing a 95–98% $N_2$/5–2% $H_2$ atmosphere. Control columns were not inoculated with strain PsKC.

Inoculation and evaluation of cell breakthrough under aerobic conditions was performed with nutrient broth-grown (aerobic columns and glass bead columns) cultures which were harvested by centrifugation (10', 10,000× g, 15° C.) and resuspended in 5 mL of 5 mM phosphate buffer (pH 8). A one milliliter cell suspension ($10^{10}$ cfu/mL) containing 10 mg/L bromide was loaded on each column. Inoculation and breakthrough of strain KC cells under denitrifying conditions was performed using cultures grown in medium D, harvested by anaerobic centrifugation in sealed Oakridge style centrifuge tubes and resuspended to $10^9$ cfu/mL in anaerobic 5 mM phosphate buffer (pH 8). One mL of anaerobic cell suspension containing 10 ppm bromide was loaded on each column. Columns were exchanged with CT-free model groundwater at 2.5 mL/min, and 5 mL fractions were collected and assayed for cells by optical density and plate counts. Bromide was assayed by ion chromatography.

Following inoculation, anaerobic Ottawa sand and glass bead columns were incubated for 5 days at 20° C. During this time, five pore volumes of medium D were exchanged through the columns to ensure sufficient nutrients for colonization. After colonization, all exchanges used CT-contaminated groundwater (20–30 μg/L CT) which was previously "niche adjusted" by addition of NaOH to raise the pH to 8.2, and supplemented with 2.8 mM acetate and 0.1 mM phosphate. Columns were exchanged at 2.5 mL/min, and 5 mL fractions were collected and assayed for CT.

Figure 6:
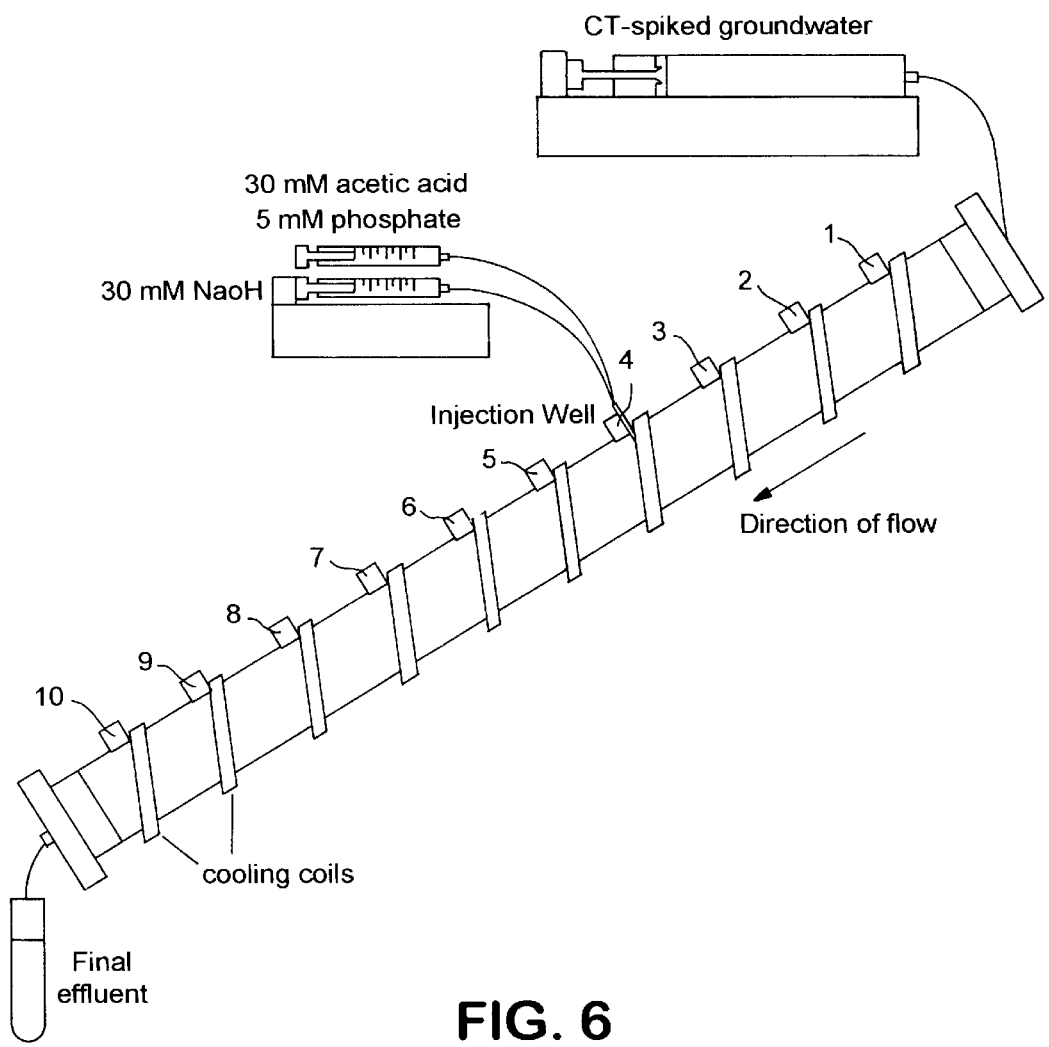
FIG. 6 is a schematic front view of a continuous flow model aquifer system.

Continuous flow model aquifer. As illustrated in FIG. 6, a continuous flow model aquifer system was constructed to evaluate the feasibility of long-term colonization, niche adjustment, and CT-transformation and strain PsKC under non-sterile operating conditions. The model aquifer was constructed with a Pharmacia FPLC, Piscataway, N.J. guard column (1 meter ×5.4 cm diameter) packed with Ottawa Sand and outfitted with injection/sampling ports ("wells") consisting of 1/4"NPT-1/4"Swagelock unions fitted with 10/32" Thermogreen GC septa (Supelco, Bellefonte, Pa.) installed at 3"intervals along the length of the column. The resulting model had a pore volume of 520 mL, a total volume of 1360 mL, and an observed porosity of 0.38. Cooling coils were used to maintain a temperature of 20° C. The system was presaturated with CT at 20–30 μg/L by pumping non-sterile groundwater from the Schoolcraft aquifer through the system at a flowrate approximating flow conditions in the Schoolcraft aquifer (linear velocity of 15 cm/day, 50 μL/min). This process continued until a steady level of effluent CT was obtained (26 days), indicating equilibration of the solid and aqueous phase CT.

Alkaline niche adjustment and maintenance of the niche was performed at well #4. Niche adjustment was achieved by injecting a mixture of 30 mM acetic acid, 5 mM potassium phosphate, and 30 mM NaOH into well #4 via a Harvard syringe pump (1–2 μL/min) beginning on day 26. After 10 days of niche adjustment, 6×$10^9$ strain PsKC cells (2 mL o/n nutrient broth grown culture) were introduced into the model aquifer at well #5. CT levels were monitored by extracting groundwater samples at upstream and downstream wells. After 65 days, levels of colonization by strain PsKC were determined by MPN dilutions and scoring for CT degradation in the absence of chloroform.

Figure 7:
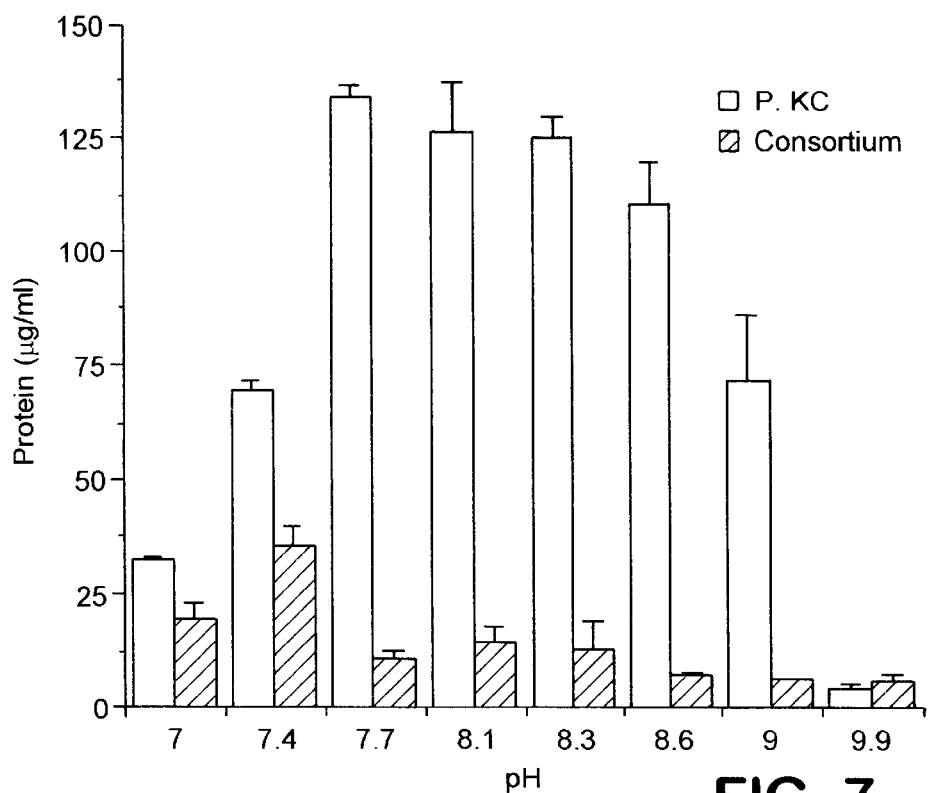
FIG. 7 is a graph showing the effect of initial medium pH on growth yield of Pseudomonas sp. strain PsKC and Schoolcraft aquifer microbial flora. Values represent the average of triplicate cultures, and the error bars indicate the standard deviations.

Effect of pH on Persistence and growth of strain KC. As shown in FIG. 7, initial medium pH had a significant effect on the concentration of protein produced in medium D. The effect of medium pH on the Schoolcraft aquifer native microbial flora are shown for comparison. Highest protein concentrations for strain PsKC were obtained in the moderately alkaline range. This demonstrates that growth of strain PsKC is optimal under alkaline conditions. The Schoolcraft microbial flora showed a pH optimum for growth in the neutral range (pH 7–7.4). Reduced growth of PsKC at pH levels less than 8.0 are likely related to specification changes that increase the toxicity of copper (Criddle, C. S., et al., Appl. Environ. Microbiol. 56:3240–3246 (1990)). Changes in the speciation and solubility of iron and cobalt may also have affected protein production (Criddle, C. S., et al., 56:3240–3246 (1990); Tatara, G. M., et al., Appl. Environ. Microbiol. 59:2126–2131 (1993)).

Figure 8:
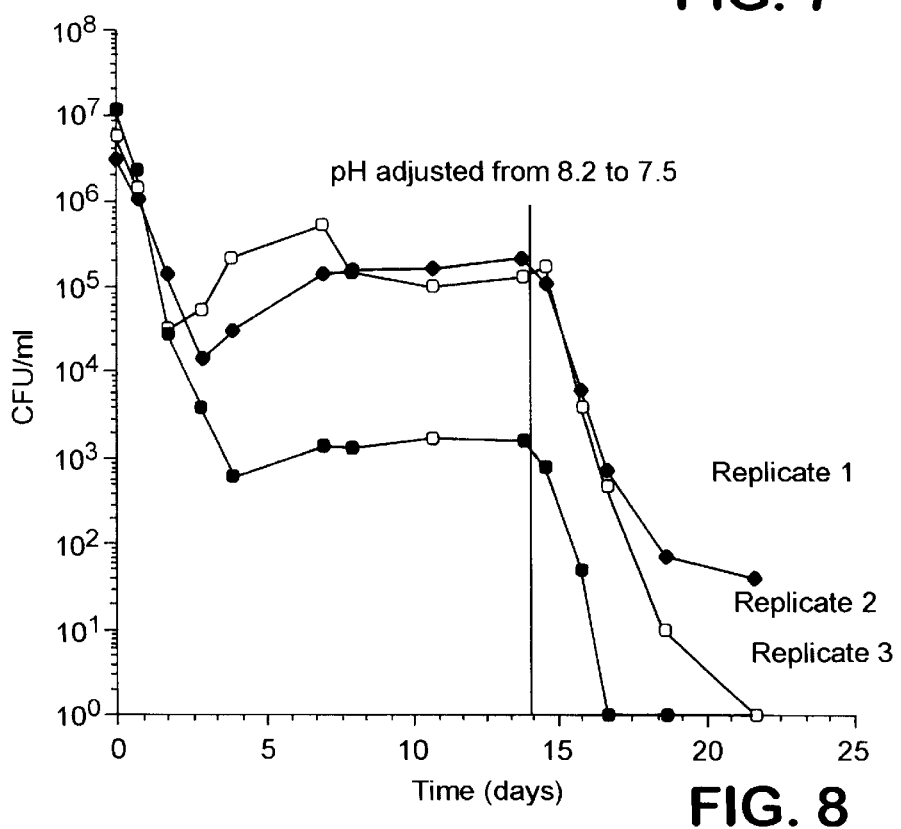
FIG. 8 is a graph showing the persistence of strain PsKC under non-growing conditions in Schoolcraft groundwater at pH 8.2. After 2 weeks incubation, the pH was reduced to 7.5.

The persistence of strain PsKC under non-growing conditions (no electron acceptor or donor) also demonstrates a pH dependence (FIG. 8). A stable population of strain PsKC (103–105 cfu/ml) rapidly decayed upon a shift of pH from 8.2 to 7.5, resulting in a drop of 3 orders of magnitude in the population levels of strain PsKC in 7 days.

EXAMPLE 6

Figure 9:
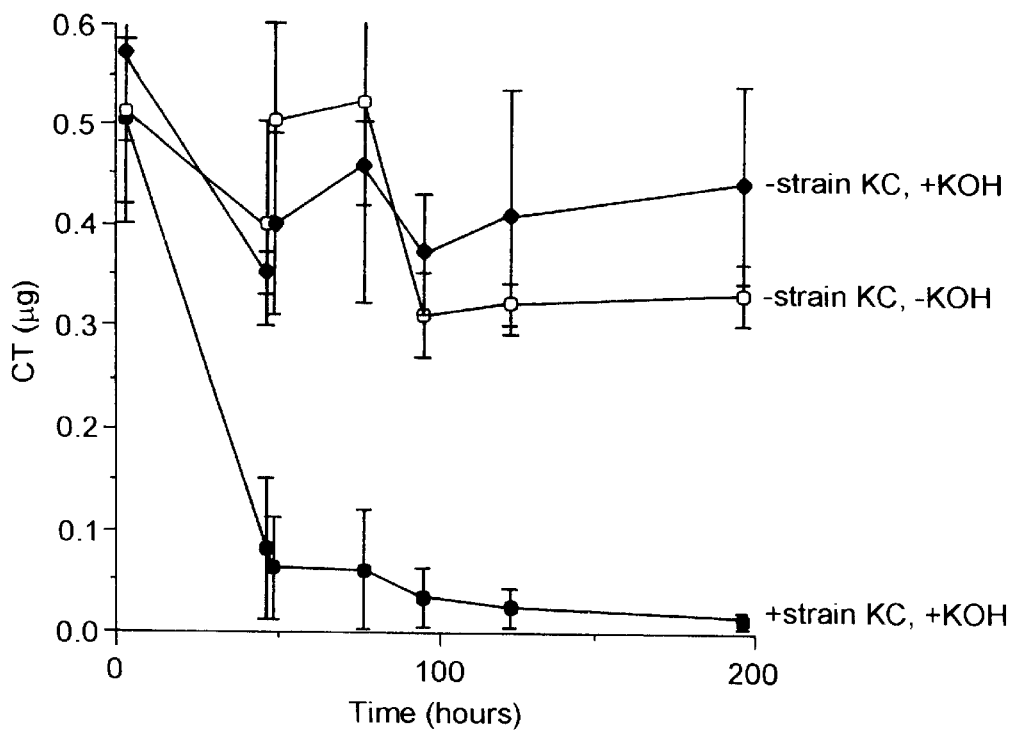
FIG. 9 is a graph showing the effects of alkaline niche adjustment on CT transformation in Schoolcraft groundwater. +strain KC=1% inoculum of strain PsKC. +KOH =pH adjusted to 8.2 with KOH. Values represent the average of triplicate samples, and the error bars indicate the standard deviations.
Figure 10:
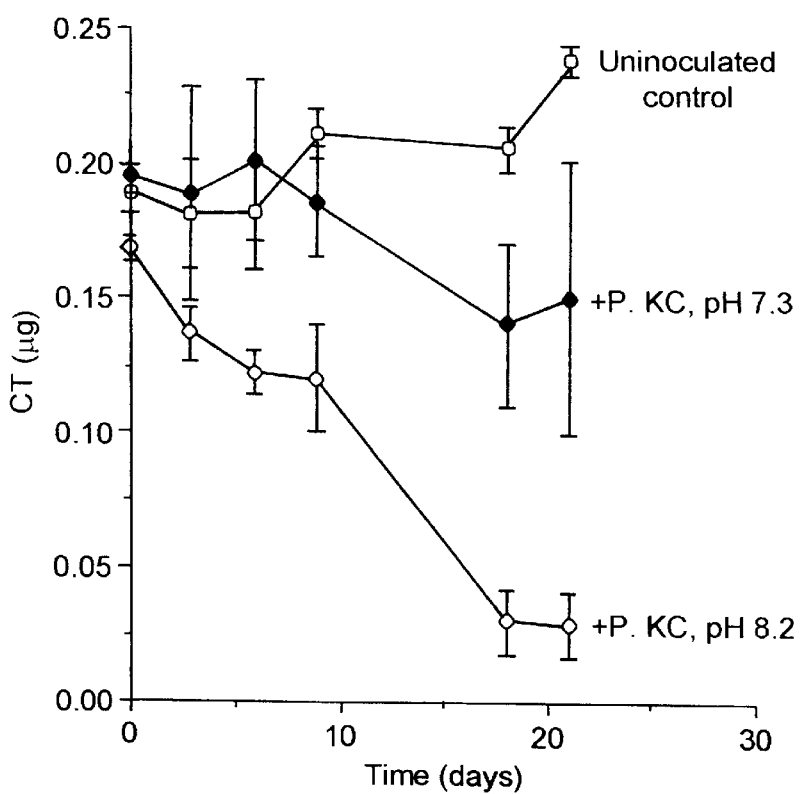
FIG. 10 is a graph showing the effects of alkaline niche adjustment on CT transformation in B horizon soil. pH 7.3 and pH 8.2 samples were inoculated with 1% (vol/vol) 24 hour nutrient broth grown cultures of strain PsKC. Values represent the average of three triplicate cultures, and the error bars indicate the standard deviations.

CT transformation in groundwater and soil systems. To determine the effectiveness of alkaline niche adjustment on CT removal in non-sterile conditions, experiments were conducted with Schoolcraft groundwater and 5% Metea B horizon soil/water slurries. As shown in FIG. 9, adjustment of pH followed by addition of strain sKC resulted in rapid CT degradation in Schoolcraft groundwater. Similar results were obtained using 5% Metea B horizon soil/water slurries adjusted with KOH to pH 8.2. As shown in FIG. 10, adjusting the pH to 8.2 prior to inoculation with strain PsKC resulted in increased levels of CT degradation compared to soil slurries that did not receive pH adjustment (pH 7.3).

EXAMPLE 7

Figure 11A:
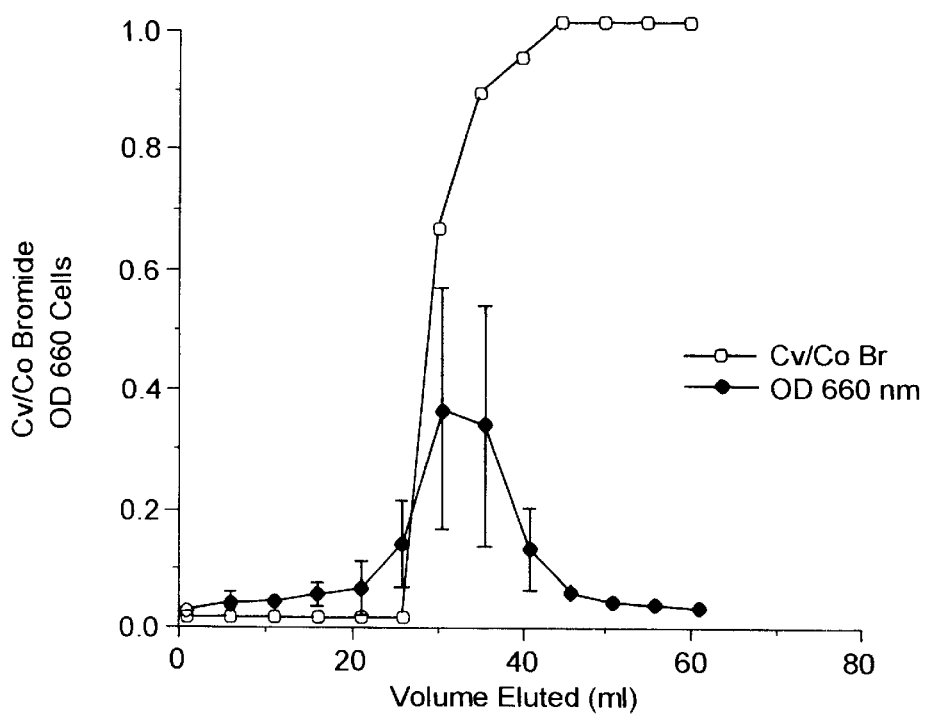
FIGS. 11A and 11B are graphs showing the elution of strain PsKC and bromide ions from aerobic Ottawa sand columns (50×1 cm). Values for cell optical density are averages of the results from 3 columns. Error bars indicate the standard deviations.
Figure 11B:
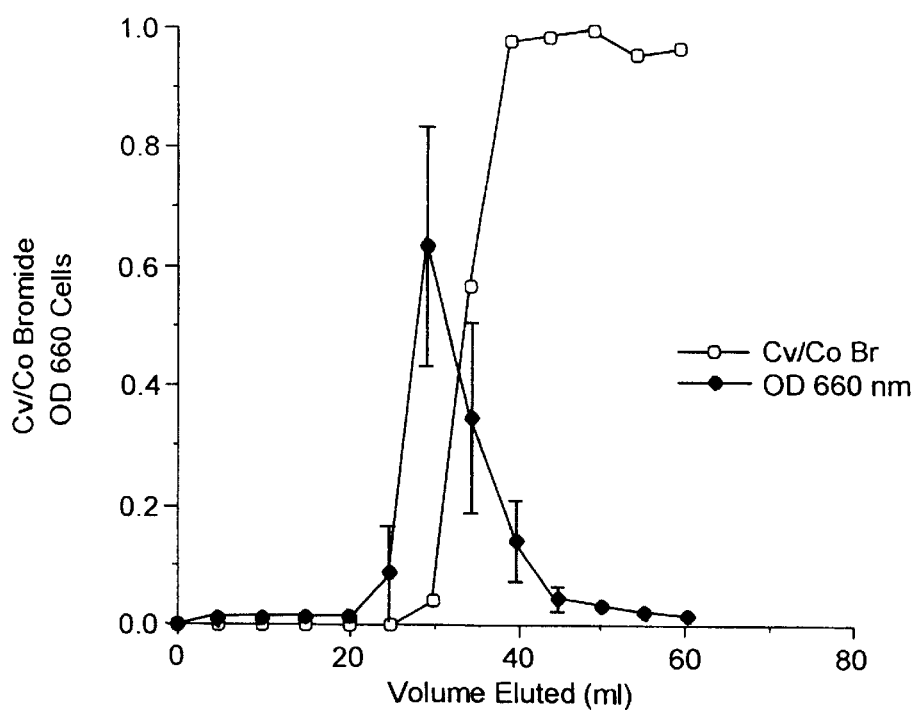

Transport of strain KC in model aquifer materials. Bromide and cell elution profiles are shown in FIGS. 11A and 11B. The results indicated that strain KC was transported up to 0.5 meter in an imposed flow field (2.5 ml/min, or ~3 cm/min linear velocity), moving ahead of the bromide tracer in the systems studied. The number of cells retained on the column was estimated by subtracting the number of cells recovered in the eluted fractions (followed by optical density and plate counts) from the number of cells loaded on the column. Approximately 20% of the cells loaded on the anaerobic Ottawa sand column were retained in the column.

EXAMPLE 8

Figure 12:
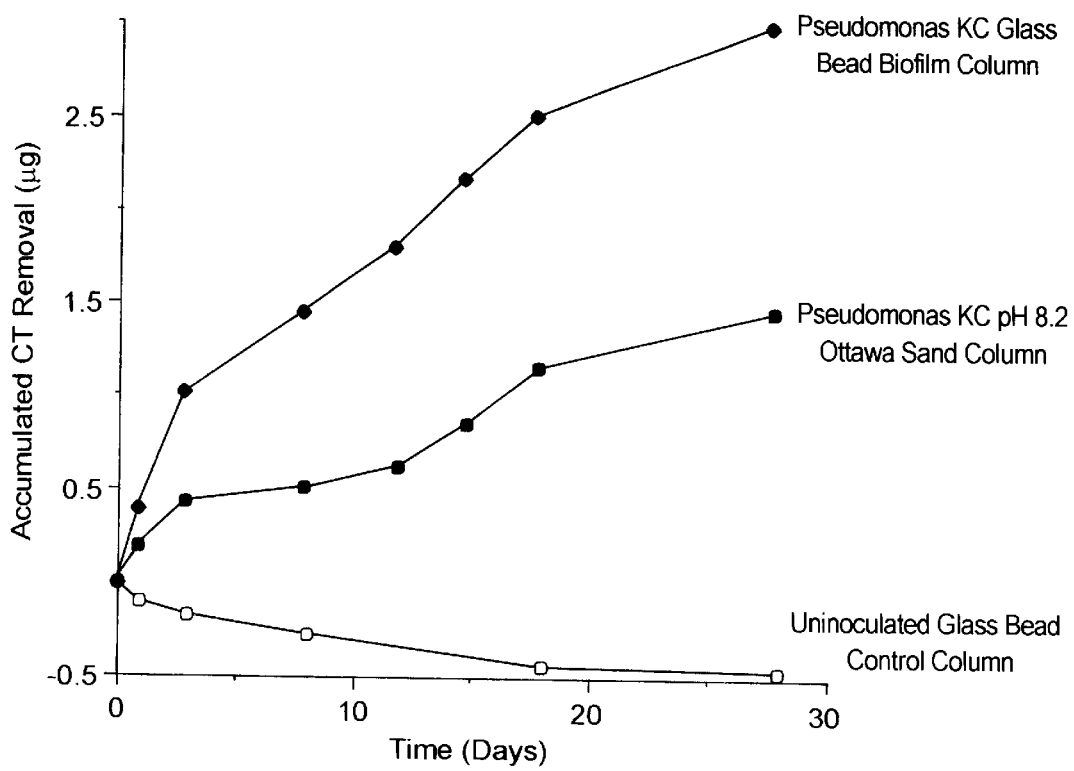
FIG. 12 is a graph showing transformation of CT by strain PsKC in glass bead or Ottawa sand columns containing groundwater from a CT contaminated aquifer. Columns were exchanged and CT levels determined as described above.

Batch exchange column CT transformation studies. The results of batch exchange column studies using Ottawa sand and glass bead columns are shown in FIG. 12. The cumulative mass of CT degraded was calculated as described by Siegrist and McCarty (Siegrist, H., et al., Journal of Contaminant Hydrology 2:31–50 (1987)). Substantial CT degradation was observed in both the Ottawa sand and glass bead columns inoculated with strain KC. No degradation was observed in the uninoculated control column, however, the mass balance for CT in the control column showed an apparent "production" of CT, an artifact caused by slight losses of CT from groundwater samples used in the exchanges.

EXAMPLE 9

Figure 13:
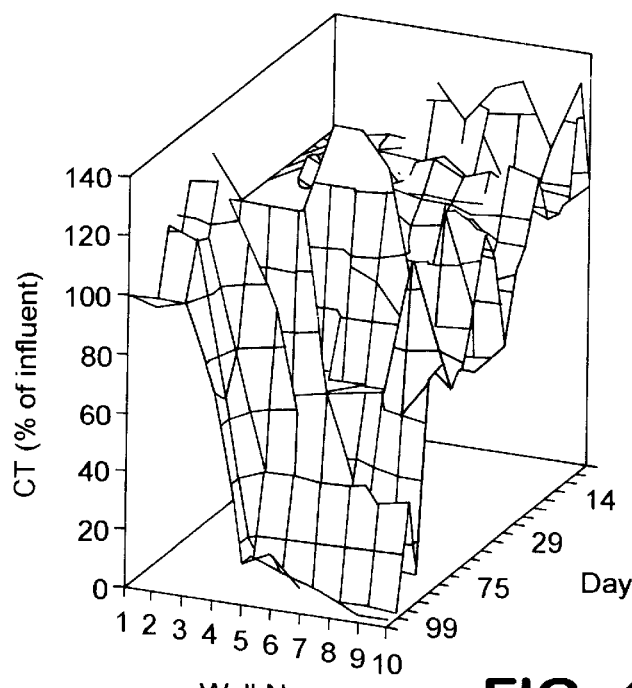
FIG. 13 is a graph showing effects of alkaline niche adjustment on CT transformation in a continuous flow model aquifer. Well positions are indicated in FIG. 6. The column was operated for 26 days to equilibrate CT levels and allow colonization by indigenous microbial flora. Acetate, base and phosphate addition was initiated on day 26. Strain PsKC cells ($5.8 \times 10^9$) were added on day 36 at well #5.

Continuous flow column studies. A continuous flow model aquifer system (FIG. 6) was operated as described in Materials and Methods. Changes in CT concentration at different sampling wells along the length of the model aquifer are indicated in FIG. 13. Key operational changes, such as the initiation of alkalinity addition for niche adjustment (day 26) and inoculation (day 36), are also indicated. As illustrated in FIG. 13, CT removal proceeded rapidly following inoculation of strain PsKC. In addition, a CT-removing zone was established between wells 5–10. Ninety to ninety-five percent of the CT entering the CT-removing zone was removed (inflow concentration 20–30 ppb).

To determine the levels of colonization by strain KC in the model aquifer, groundwater samples at wells 1–10 were extracted on day 101 (65 days after inoculation), serially diluted into medium D and screened for CT degradation. The results (Table 4) indicate that strain KC was present at well positions 5–10, with highest levels in the vicinity of well 5,(inoculation site).

TABLE 4

Strain KC in the continuous flow
model aquifer system on day 101

| Well Number | Pseudomonas KC CFU/mL of extracted groundwater[1] |
|---|---|
| 1 | 0 |
| 2 | 0 |
| 3 | 0 |
| 4 | niche adjustment well |
| 5 | $10^7$ |
| 6 | $10^5$ |
| 7 | $10^4$ |
| 8 | $10^2$ |
| 9 | $10^2$ |
| 10 | $10^2$ |

[1]lowest dilution showing growth, CT degradation, and no CF production.

Taken together with other observations of growth and CT transformation reported here, it is concluded that alkali niche-adjustment is a useful means of maintaining a competitive population of strain KC under non-sterile operating conditions.

EXAMPLE 10

This example shows transformation of CT in 50% Hanford aquifer solids slurries. Samples were prepared under argon in simulated groundwater containing 16 g/l acetate and nitrate at pH 6.7 or 8.2 and inoculated with $10^5$ Pseudomonas KC per gram.

TABLE 5

| | $\mu$g CT remaining after 5.8 days* | |
|---|---|---|
| | pH 6.7 | pH 8.2 |
| uninoculated control | 0.25 ± 0.01 | 0.21 ± 0.07 |
| HC-14 added | 0.29 ± 0.07 | 0.27 ± 0.01 |
| PsKC added | 0.21 ± 0.05 | 0.01 ± 0.00 |

*determined by headspace measurement after heating samples to 70° C. for one hour to "bake off" sorbed CT.
±one standard deviation.

The results show that the PsKC is very effective at pH 8.2.

The concept of niche adjustment has broad implications for bioaugmentation efforts, where competition with native microorganisms is a major hurdle. Addition of alkalinity is a simple procedure that may be effective at certain sites. However, other niche adjustment strategies can be envisioned. The optimal choice of strategies will depend upon the physiology of the organism to be introduced, the nature of the indigenous organisms, and prevailing environmental conditions at a targeted site.

EXAMPLE 11

Bench-scale laboratory methods were used to evaluate the feasibility of bioaugmentation with strain PsKC to remediate aquifer materials from an aquifer of documented CT contamination at Schoolcraft, Mich. Nine glass columns packed with uncontaminated aquifer materials from the site were used to simulate aquifer conditions. Columns were alternately exchanged with groundwater from the site in a rapid (20–30 minute) displacement of the pore fluid then incubated under static conditions for a period of days to weeks. The exchange and incubation procedure continued until CT removal began to plateau, indicating equilibration of the sorbed CT with CT in the pore fluid. Information obtained during this period was used to evaluate porosity and CT sorption. In subsequent exchanges, base, acetate, and phosphorus were added to the exchange fluids to create conditions favorable for growth of strain PsKC and expression of its CT transformation activity (niche adjustment). Three columns were inoculated with strain PsKC; three were not inoculated; and three were chemically disinfected with thimersol. Strain PsKC was transported more rapidly than the average linear velocity of the exchange fluids in the inoculated columns. Protein levels measured in the effluent of the inoculated columns during subsequent exchanges indicated that niche adjustment enabled rapid growth and colonization of the aquifer solids by strain PsKC. Little or no protein was detected in the effluent of uninoculated columns. CT mass balances on the inoculated, non-inoculated, and chemically-disinfected columns indicated that niche adjustment and inoculation with strain PsKC created conditions favorable for CT removal from the aquifer solids. Up to 70% removal of soluble CT (30–50$\mu$g/L) occurred in inoculated columns over a period of 7 to 9 days.

The experimental method used is an extension of the method originally developed by Siegrist and McCarty (Siegrist, H., et al., Journal of Contaminant Hydrology, Vol. 2, pp. 31–50 (1987)). Nine columns packed with Schoolcraft aquifer materials and saturated with groundwater from the site were prepared. These columns were exchanged with groundwater from the site in a rapid (20–30 minute) displacement of the pore fluid then incubated for a period of days to weeks under static conditions. This exchange and incubation procedure was repeated until CT removal began to plateau, indicating equilibration of the sorbed CT with CT in the pore fluid (at least two successive exchange events were executed without significant differences between influent and effluent CT concentrations). Information obtained during this period was used to evaluate porosity and CT sorption. In subsequent exchanges, the niche was adjusted by addition of base, acetate, and phosphorus to create conditions favorable for growth of strain PsKC and expression of its CT transformation activity. Three columns (column set 1) were inoculated with strain PsKC; three (column set 2) were not inoculated and three (column set 3) were chemically disinfected with thimersol.

The experiment was conducted in three phases: (1) determination of porosity by tracking bromide and CT breakthrough curves for each of the nine columns during the initial exchanges, (2) evaluation of sorption during initial incubation periods, and (3) assessment of niche adjustment and bioaugmentation with strain PsKC. In the first exchange event of the final phase, each column received groundwater that was adjusted to pH 8.1 and supplemented with phosphate. Subsequently, in the second exchange of the final phase, an inoculum containing strain KC was introduced into column set 1. At the same time, the groundwater used for exchanges of all three column sets was supplemented with acetate. Acetate, base, and phosphate supplements continued throughout the remainder of the experiment.

Aquifer Material

Aquifer material for column preparation was obtained through hollow stem augers following Standard Penetration Test procedures (ASTM-D-1586-84). The boring from which the aquifer samples were collected was located approximately 50 feet downgradient of Michigan Department of Natural Resources (MDNR) monitoring well VS-MW-35, near the inferred center of mass of Plume A. At this location, the augers were advanced to a depth of 23 feet below grade (approximately 8 feet below the water table). Samples of aquifer solids then were acquired using split-barrel core sampling devices (18 inches in length, 2 inches in diameter) inserted through, and driven beyond, the terminal depth of the augers. A total of three samples were collected from a continuous interval between 25 and 29.5 feet below grade. Upon acquisition, cubic centimeter samples of soil and associated pore fluids were extracted from each core using sterilized 10 mL syringes that had been cut to remove their needle adapters and create a larger opening through which to acquire sample. The remaining mass of soil from the cores was transferred to sterile glass mason jars and packed on ice for transport. Prior to drilling and sample acquisition, the hollow stem augers and split barrel sampling devices were sterilized by high pressure steam.

Groundwater

Groundwater for column exchanges was obtained from monitoring well VS-MW-05, located within, and approximately 800 feet upgradient of the center of mass of Plume A. Before sample acquisition, approximately 50 gallons of groundwater were purged from the well using a suction pump to ensure that the groundwater sampled was representative of ambient aquifer conditions. Sample collection consisted of filling as many as two 5 gallon NALGENE carboys with water withdrawn from the well using TEFLON bailers. Each carboy was filled completely to eliminate headspace within the container. The carboys were then placed on ice for transport to the laboratory where they were stored at 4° C. Periodically, an aliquot of groundwater was removed from the carboy and used to measure concentrations of nitrate, nitrite, iron and CT.

Column Preparation

Nine KONTES glass columns (30 cm length, 2 cm inside diameter) fitted with TEFLON leur lock stopcocks were sanitized by soaking in a solution of 0.065 hypochlorite, rinsed with sterile distilled water, and packed aseptically in a laminar hood with a slurry of Schoolcraft aquifer solids in degassed (e.g. CT-free) Plume A groundwater. The columns were periodically tapped during the filling process to enhance packing. Each column was connected to external TEFLON plumbing consisting of influent and effluent liquid transfer tubing and appurtenances necessary to make direct connections to a syringe pump. Once packed columns were refitted with external plumbing and placed in a chamber at 10° C. to simulate aquifer conditions. The columns were then connected to a Harvard syringe pump. For a period of several hours, CT-free, Plume A groundwater was exchanged through each column to remove small bubbles and reduce dissolved oxygen concentrations in the column.

Preparation of Exchange Fluids and Calibration Standards

Effluent fractions generated during each exchange of pore fluid were collected in 28 mL glass Balch tubes sealed with TEFLON-lined butyl rubber septa. By inserting a hypodermic needle through the septa and withdrawing 5 mL of air, a vacuum was created in each tube just prior to sample collection preventing pressurization of the tubes during sample collection.

To prepare calibration standards for each exchange event, five Balch tubes were injected with 5 mL of CT-free (air stripped) Schoolcraft groundwater. Standard stock solution (8.3 $\mu$g CT/mL methanol) were then added to four of the five tubes in 5, 10, 20, and 30 $\mu$L aliquots, respectively. The fifth tube served as a CT-free blank.

After preparation of calibration standards, approximately 300 mL of Plume A groundwater was transferred from sample carboys to a sterilized glass beaker. Niche adjustment and substrate/nutrient addition was accomplished by transferring 0.55 mL of 0.1 M NaOH, 1.8 mL of 0.1 M sodium acetate, and 0.3 mL of 0.1 mM $KH_2PO_4$ solution from sterile serum bottles to the beaker. The resulting solutions (pH 8.1, 0.59 mM acetate, 0.099 mM phosphate phosphorus) were then mixed aseptically and transferred to two 250 mL TEFLON syringes. Column set 3 (chemically inhibited control columns) also received 200 mg/L of Thimersol.

Exchange Protocol

Syringes were loaded into the syringe pump and connected to the external plumbing of the column set to be exchanged. The pump was then activated and groundwater pumped through the influent transfer lines at a rate of 2.5 mL/min. To ensure that these lines were adequately flushed of prior exchange fluids, and to quantify the initial concentration of CT in the influent groundwater, up to three 5 mL samples of the groundwater were collected prior to initiating the pore fluid exchange within the first column of a set. This was accomplished by disconnecting the influent transfer line from the third column of the set and attaching a hypodermic needle to facilitate injecting the groundwater through the septa of the sample tube. After sampling, the influent line was reconnected. The stopcocks on the top and bottom of the first of the three columns in the set were then opened, and the exchange of fluid initiated.

During exchanges, 60 to 65 mL of groundwater were pumped through each column at a rate of 2.5 mL/min. Effluent samples were collected in 5 mL fractions in the sealed, evacuated Balch tubes.

Inoculation

Inoculation of column set 1 was performed in a single exchange event. Column set 2 was "mock inoculated"

following similar procedures. Inoculation entailed injecting a 1 mL suspension of strain KC cells directly into each of the three columns prior to the exchange of pore fluids. This was accomplished by attaching a sterile 1 mL syringe containing the suspension ($4.7 \times 10^{10}$ cells of strain KC in 100 mM $KH_2PO_4$ buffer pH 8.0) to the influent transfer line for each column, and quickly dispensing the inoculum. Immediately following inoculation, the transfer lines were reattached and exchange of groundwater commenced. "Mock inoculation" of column set 2 was accomplished in the same manner as inoculation in column set 1, but the inoculum consisted only of 100 mM $KH_2PO_4$ buffer, pH 8.0. Effluent fractions were acquired aseptically by sterilizing with ethanol swab the septa on each Balch tube and the hypodermic needles used to transfer pore fluids from the columns to the tubes.

Analyses and Enumeration

CT and CF concentrations were measured in all effluent fractions collected during this study. Initially, bromide was also measured to determine porosity and breakthrough characteristics. After niche adjustment, additional effluent analyses included pH, phosphate, protein, and strain KC cell numbers.

CT and CF were quantified by withdrawing a 0.10 mL aliquot of gas from the headspace of each fraction and calibration standard and injecting the gas sample into a Perkin Elmir model 8500 gas chromatograph equipped with a 100/120-mesh column (10% Alltech CS-10 on Chromsorb W-AW; Alltech catalog no. 12009 PC). A complete description is provided by Tatara et al (Tatara, G. M., et al., Applied and Environmental Microbiology. vol. 59, no. 7, pp. 2126–2131 (1993)). When possible, headspace analyses were performed within a half hour of sample acquisition. Occasionally, circumstances required overnight storage (at 4° C.) before analysis. Of these samples, all were analyzed within 24 hours of collection. Bromide and phosphate were measured by ion chromatography (Dionex model 2000i/SP ion chromatograph with suppressed conductivity detection equipped with a Sarsep AN 300 anion exchange column and utilizing a 1.8 mM bicarbonate/17 mM carbonate mobile phase at 1 mL/min). Chromatographs were recorded and data integrated using a Spectra Physics model SP 4270 integrator. External standard calibration curves were prepared by diluting primary ion standards into secondary water standards with the same ionic composition as the test samples.

Measurements of pH were obtained with an Orion model 720A pH meter. Protein was determined by the modified Lowry method, with bovine serum albumin as the standard (Markwell, M. A., et al., Methods Enzymol. vol 72, pp. 296–301 (1981)). Cell numbers were estimated by serial dilution/standard plate count methods and verified by most probable number analysis (MPN).

Mass Balances

In order to evaluate the fate of CT, mass balances were performed using effluent concentrations for each exchange event. The analysis follows the protocol of Siegrist and McCarty (Siegrist, H., et al., Journal of Contaminant Hydrology, vol. 2, pp. 31–50 (1987)), with minor modifications.

Figure 14:
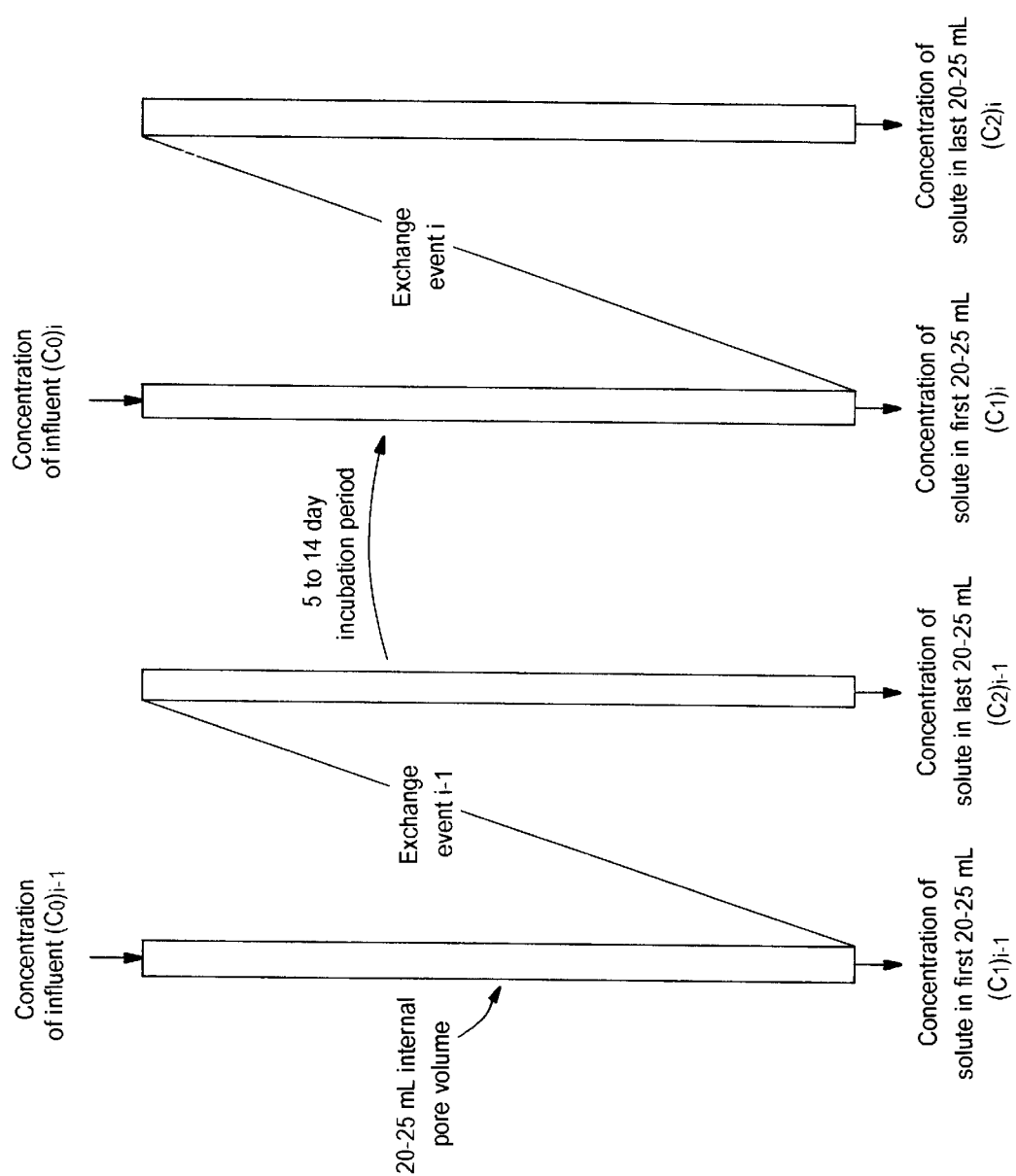
FIG. 14 is a schematic view showing a column exchange.

FIG. 14 illustrates key concentration and volume relationships important in this analysis, $C_1$ is the CT in the column pore fluid prior to exchange. $C_2$ is the concentration of CT in the pore volume at the conclusion of the exchange, following breakthrough. $C_0$ is the concentration of the influent for each exchange.

During the initial exchange of fluids in each column, breakthrough of both bromide and CT were evaluated. For this first exchange, $C_1=0$. Using the bromide data, the porosity, e, of the aquifer media within each column was calculated by:

$$\varepsilon = \frac{M}{(C_2 - C_1)} \left( \frac{1}{V_{column}} \right) = \frac{V_{pore}}{V_{column}}$$

when $C_2 = C_O = C_{column}$, and $M = C_{column} V_{column}$ $_{\varepsilon = C2} V_{pore}$. Unlike bromide, CT was sorbed to the aquifer solids during exchange. CT also underwent more dispersion than bromide. These two mechanisms were reflected in the shape of the CT breakthrough profile, which lagged behind and sloped less than the profile for bromide (FIG. 3). Analysis of the CT data indicated that a minimum exchange volume of 45–50 mL was required for complete breakthrough.

Mass removal between exchange events was assumed to be the result of either sorption or biotransformation. Thus, to determine the cumulative mass removed between exchange events, it was only necessary to know the concentration in the effluent at the end of an exchange event $(C_2)_i$ and the concentration exiting the column at the beginning of the next exchange event $(C_1)_i$. These data enabled estimation of cumulative mass removal between exchange events $M_r$:

$$M_r = V_{column} \varepsilon \sum_{i=1}^{n} (C_2^{i-1} - C_1^i) \quad (2)$$

Prior to inoculation and niche adjustment, information on cumulative mass removal was used to quantify sorption. Sorption was estimated by comparing the total mass of CT removed to the liquid phase concentration of CT present in the pore fluid once the solids were saturated. This ratio is defined as the dimensionless equilibrium partition coefficient, $R_p$, where:

$$R_p = \frac{M_r}{M_{dissolved}} = \frac{V_{column} \varepsilon \sum_{i=1}^{n} (C_2^{i-1} - C_1^i)}{V_{column} \varepsilon C_1^i} \quad (3)$$

With knowledge of $R_p$, the retardation factor, $_tR$, and distribution coefficient, $K_d$ ($cm^3/g$), for CT in the Schoolcraft aquifer materials could be estimated from:

$$R_t = \frac{v_{eff}}{v_{contaminant}} = R_p + 1 \quad (4)$$

$$K_d = \frac{R_p \varepsilon}{\varrho_b} \quad (5)$$

where $V_{eff}$=average linear velocity of groundwater flow through the aquifer solids within the column (cm/hr) $V_{contem}$=the average linear velocity of the solute front in the aquifer solids within the column (cm/hr) Qb=soil bulk density ($g/cm^3$)

Kinetics of Biotransformation

Tatara et al (Tatara, G. M., et al., Applied and Environmental Microbiology, Vol. 59, No. 7, pp. 2126–2131 (1993)) showed that the transformation of CT by strain KC is first order with respect to the solute concentrations within the range evaluated during this study (30–50 µg/L). Assuming a first-order kinetic expression and equilibrium between the sorbed and dissolved phases, the following mass balance can be obtained:

$$-\frac{dM_{CT}}{dt} = k'' C_{liquid} V_{column} \varepsilon = k'' \left( \frac{M_{CT}}{V_{liquid} + K_d M_{soil}} \right) V_{liquid} \quad (6)$$

$$\ln\left(\frac{M_{CT}^i}{M_{CT}^{i-1}}\right) = -\left(\frac{k'' V_{column} \varepsilon}{V_{column} \varepsilon + K_d M_{soil}}\right) t \quad (7)$$

where K"=apparent first order rate coefficient (day$^{-1}$) $C_{liquid}$=concentration of CT in liquid-filled volume of the column ($\mu$g/L) $M_{CT}$=Mass of CT within column at (i-1) and i ($\mu$g) $M_{soil}$=Mass of soil in column (g) t=time interval between (i-1) and i (days)

Characterization of Aquifer Materials

Table 6 summarizes selected physical and chemical characteristics of the Plume A groundwater and Schoolcraft aquifer solids.

TABLE 6

Characteristics of Schoolcraft Aquifer Materials

| PARAMETER | MEDIA | |
|---|---|---|
| | SOIL | GROUNDWATER |
| pH | 8.8 | 7.04–7.5 |
| Alkalinity (mg/L as CaCO$_3$) | — | 331[1] |
| Hardness (mg/L as CaCO$_3$) | — | 410[1] |
| Fraction of Organic Carbon (%) | .1 | — |
| Iron (mg/L) | 37 | 11 |
| Copper (mg/L) | — | .03[1] |
| Nitrate (mg/L) | ND | 39 |
| Nitrite (mg/L) | ND | 0 |
| Phosphate (mg/L) | — | 60[1] |
| Sulfate (mg/L) | — | 16[1] |
| Carbon Tetrachloride ($\mu$g/L) | ND | 30–50 |
| Microbial Population | 2.3 × 10$^7$ CFU/g | 1 × 10$^8$ CFU/mL |

These data indicate that the Schoolcraft aquifer materials currently support a significant microflora. In fact, it is possible that the chloroform detected in groundwater samples from one of the monitoring wells (well number VS-MW-05, HALLIBURTON NUS Environmental Corporation, 1991) may have originated from the biotransformation of CT to CF by indigenous microorganisms since alternative sources of CF are unknown.

Over the groundwater pH range reported in Table 5 (7.04–7.5), copper is toxic to strain KC (Tatara, G. M., et al., Applied and Environmental Microbiology, Vol. 59, No. 7, pp. 2126–2131 (1993)). At higher pH levels, copper is not inhibitory to cell growth and, in fact, is required for CT transformation (Tatara, G. M., et al., Applied and Environmental Microbiology, Vol. 59, No. 7, pp. 2126–2131 (1993)). In addition, iron concentrations in the groundwater (11 mg/L) are at levels inhibitory to CT transformation. As a result, growth of strain KC and associated transformation of CT required pH adjustment to reduce the solubility of copper and iron.

The concentration of nitrate (39 mg/L) in the Schoolcraft groundwater is sufficient to sustain denitrification by strain KC and support CT transformation. Although the phosphate data reported on Table 5 suggests that phosphorus is present, batch growth experiments and analysis of the groundwater used for the exchanges indicated that phosphorus was limiting microbial growth.

CT concentrations in the groundwater used for the column exchanges were consistently within the range of 30$\mu$g/L and 50$\mu$g/L. No detectable levels of CT were measured on the aquifer materials used for column preparation.

Flow-through Properties

Results of the bromide tracer experiments are presented in Table 7.

TABLE 7

Column Specifications, Flow-through Properties, and CT Sorption Characteristics

| | COLUMN BET | | | | | |
|---|---|---|---|---|---|---|
| | 1 (Inoculated) | | 2 (Non-inoculated) | | 3 (Thimereol treated) | |
| PARAMETER | Mean | +/− Std. Dev. | Mean | +/− Std. Dev. | Mean | +/− Std. Dev. |
| Column Specifications: | | | | | | |
| Length (cm) | 30 | — | 30 | — | 30 | — |
| Diameter (cm) | 2 | — | 2 | — | 2 | — |
| Empty Volume (mL) | 50 | — | 50 | — | 50 | — |
| Flow-Through Properties: | | | | | | |
| Porosity, $\varepsilon$ | .47 | .01 | .46 | .01 | .52 | .03 |
| Pore Volume, V$_0$ (mL) | 23.7 | .6 | .23 | .4 | 24.3 | 1.7 |
| Soil Bulk Density, $\rho_b$ (g/cm$^3$) | 1.4 | 0 | 1.4 | 0 | 1.4 | 0 |
| Superficial Velocity, v (mL/min) | 2.5 | 0 | 2.5 | 0 | 2.5 | 0 |
| Average Linear Velocity, v$_{eff}$ (cm/hr) | 100.9 | 2.6 | 103.8 | 1.8 | 98.6 | 7.2 |
| Dispersion Coefficient D$_{da}$ (cm$^2$/hr) | 30.3 | .8 | 31.1 | 0.5 | 29.5 | 2.1 |
| Reynolds Number, R$_0$ | .22 | 0 | .22 | 0 | .22 | 0 |
| CT Sorption Characteristics: | | | | | | |
| Dispersion Coefficient, D$_{d1}$ (cm$^2$/hr) | 151.4 | 3.9 | 155.8 | 2.8 | 147.8 | 10.8 |
| Equilibrium Partition Coefficient, R$_p$ | .82 | .34 | 1.02 | .11 | .45 | .12 |
| Retardation Coefficient, R$_t$ | 1.82 | .34 | 2.02 | .11 | 1.45 | .12 |
| Distribution Coefficient, K$_d$ (cm$^3$/g) | .28 | .11 | .33 | .04 | .16 | .05 |
| CT Biotransformation Characteristics: | | | | | | |
| Apparent First Order Rate Coefficient, k" (day$^1$) | 4.14 | .32 | — | — | — | — |

Figure 15A:
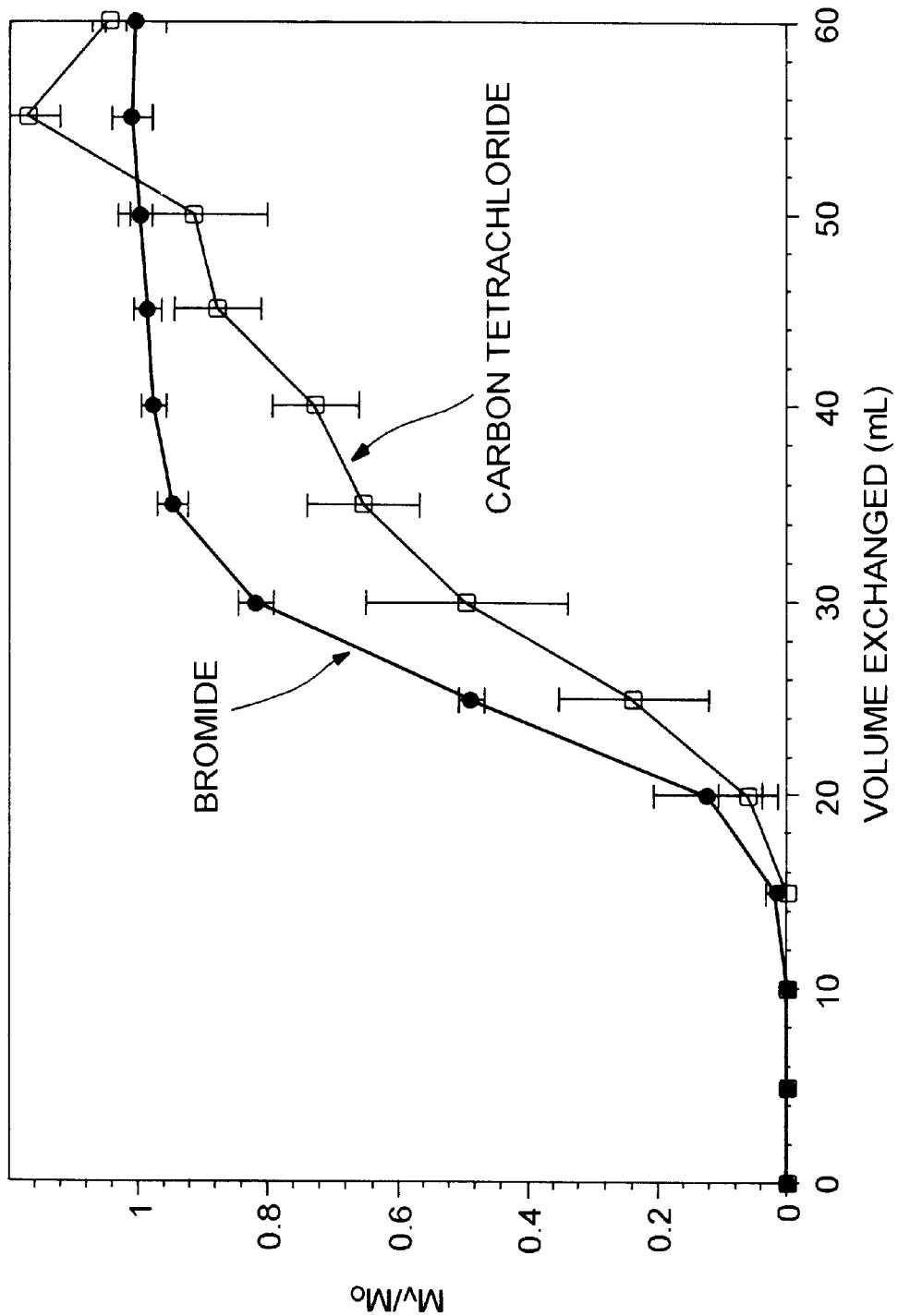
FIGS. 15A, 15B and 15C show bromide and CT breakthrough profiles: B) column set 1 (columns 1–3), B) column set 2 (columns 4–6), and C) column set 3 (columns 7–9).
Figure 15B:
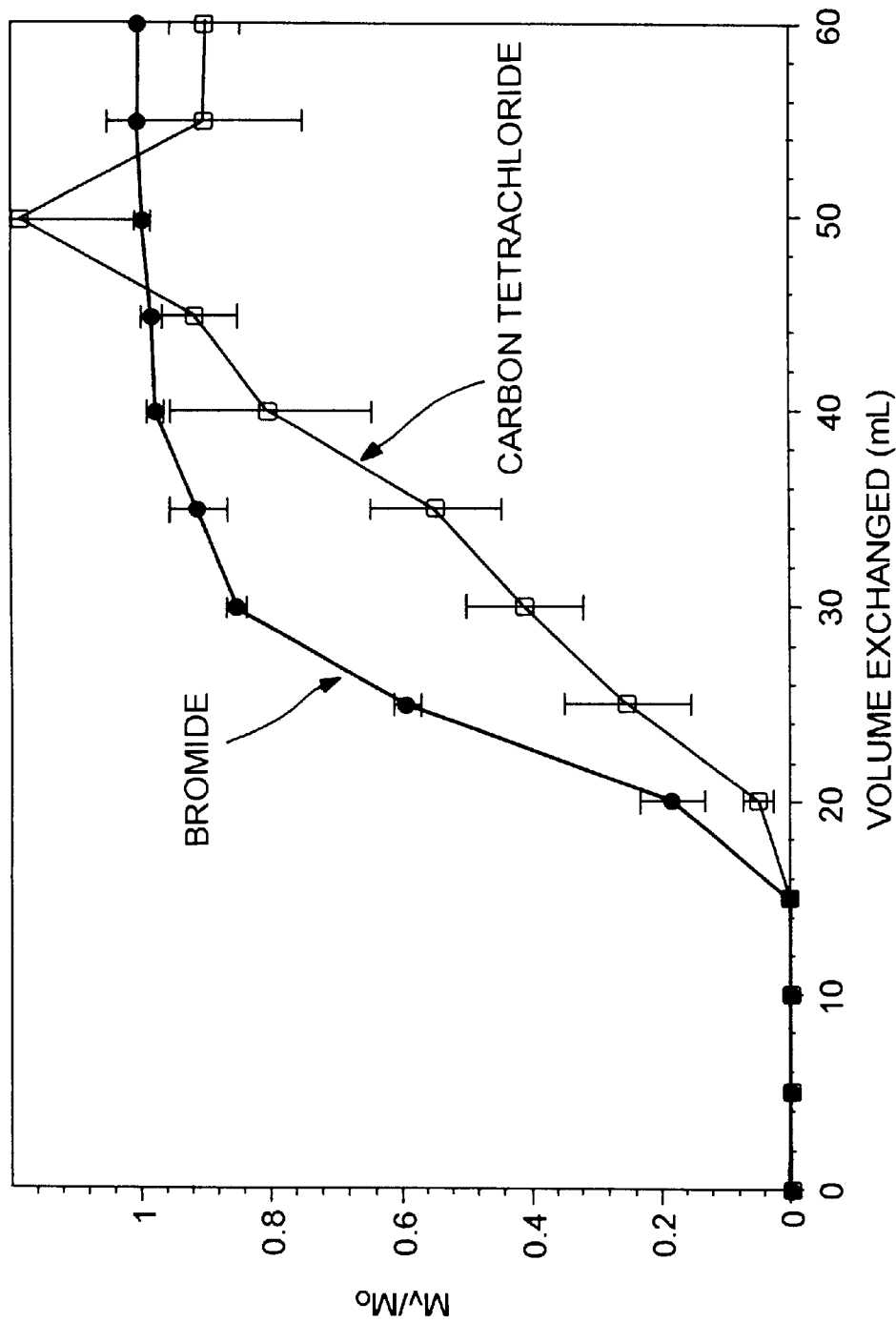
Figure 15C:
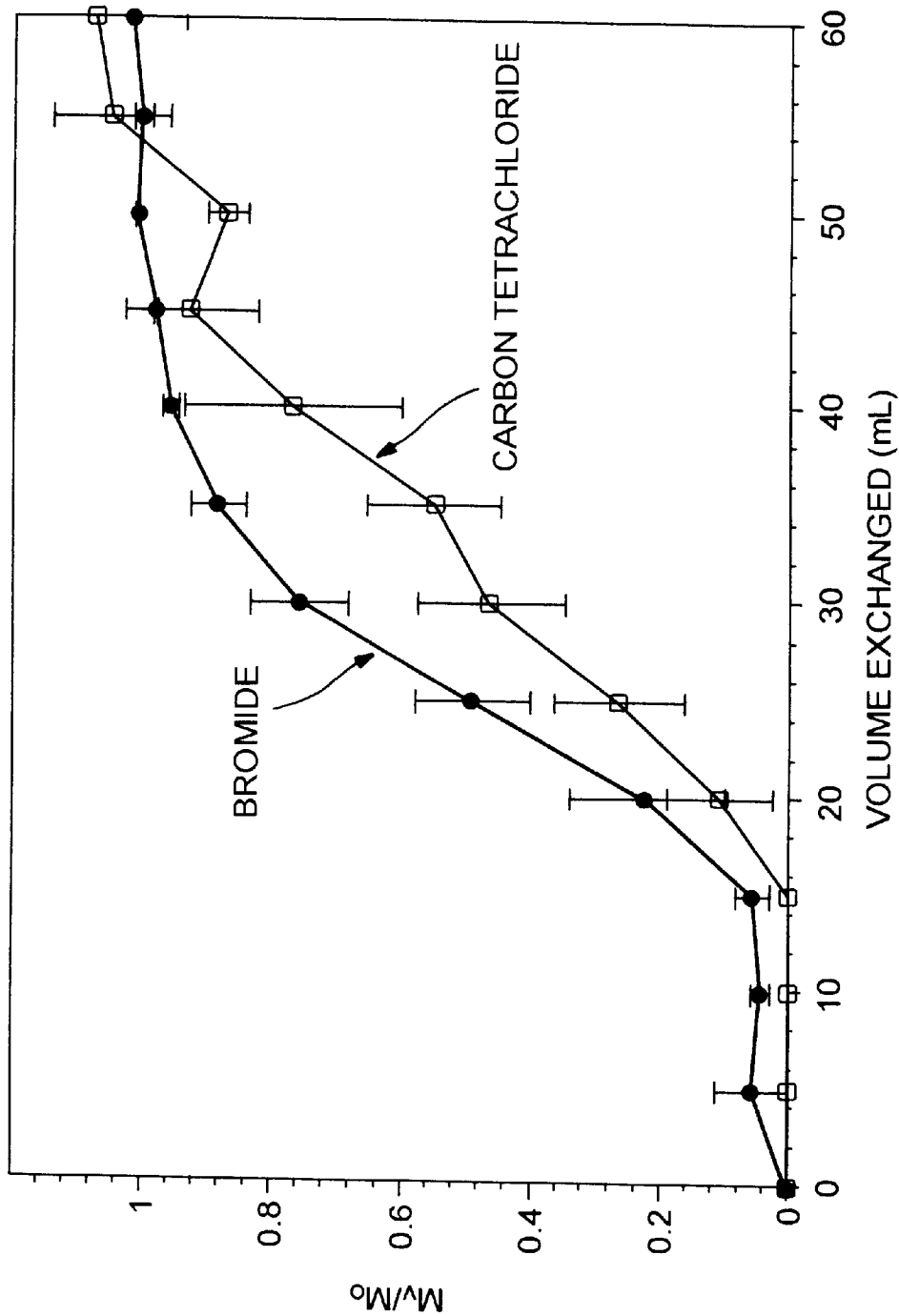

Composite bromide breakthrough profiles for each of the three column sets are presented in FIGS. 15A, 15B, 15C. The flow-through characteristics for each of the nine columns are similar. In general, the porosities of the re-packed aquifer solids within the columns were 44% to 52%, indicating internal pore volumes of 22–26 mL. The average linear velocities, $V_{eff}$, of groundwater flow during each exchange were determined from the porosity data and the superficial velocity, v (0.796 mL/min), to range from 1.53–1.81 cm/s. The Reynolds number ($R_p=vd/\mu$) was 0.133 assuming an average soil grain diameter, d, of $10^{-5}$ cm, and kinematic viscosity, $\mu$, of $3.6 \times 10^{-5}$ cm/hr at 20° C. A value of $R_p$ less than unity indicates that inertial forces dominate. Therefore, flow was essentially laminar during the exchanges (Freeze, R. A., et al., Groundwater. Prentice-Hall, Englewood Cliffs, 15–79 (1979)).

Figure 17:
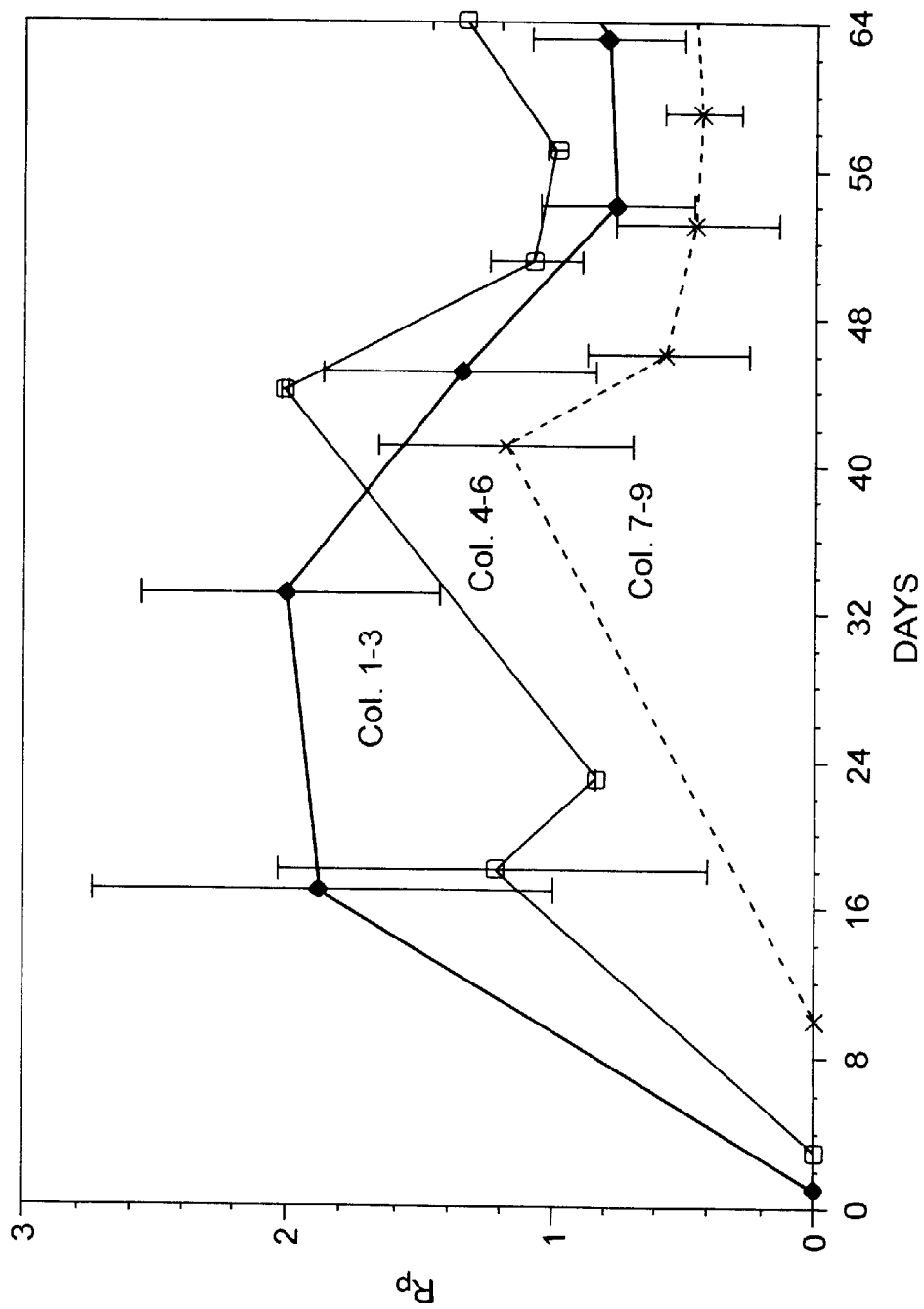
FIG. 17 shows dimensionless equilibrium coefficient, $R_p$, measured during column exchanges through saturation of each column with CT. Saturation is indicated by stabilization of $R_p$ values which generally occurred after 4–5 exchange events.

The movement of groundwater through each column deviated slightly from ideal plug flow. A composite breakthrough profile for the nine sets of tracer experiments (FIG. 17) was used to evaluate the dispersion characteristics of the aquifer solids within the columns. The first 15 mL of pore fluids exchanged was essentially free of bromide, and a total throughput of 35 mL to 40 mL of groundwater was necessary to achieve complete breakthrough, or saturation. The approximate spreading rate of the breakthrough front (as defined by the dimensionless quantity $D_{dim}/V_{eff}L$, where L is the column length) was approximately 0.01, giving a dispersion coefficient, $D_{dim}$, of less than 32 cm²/hr.

Sorption Characteristics

Figure 16:
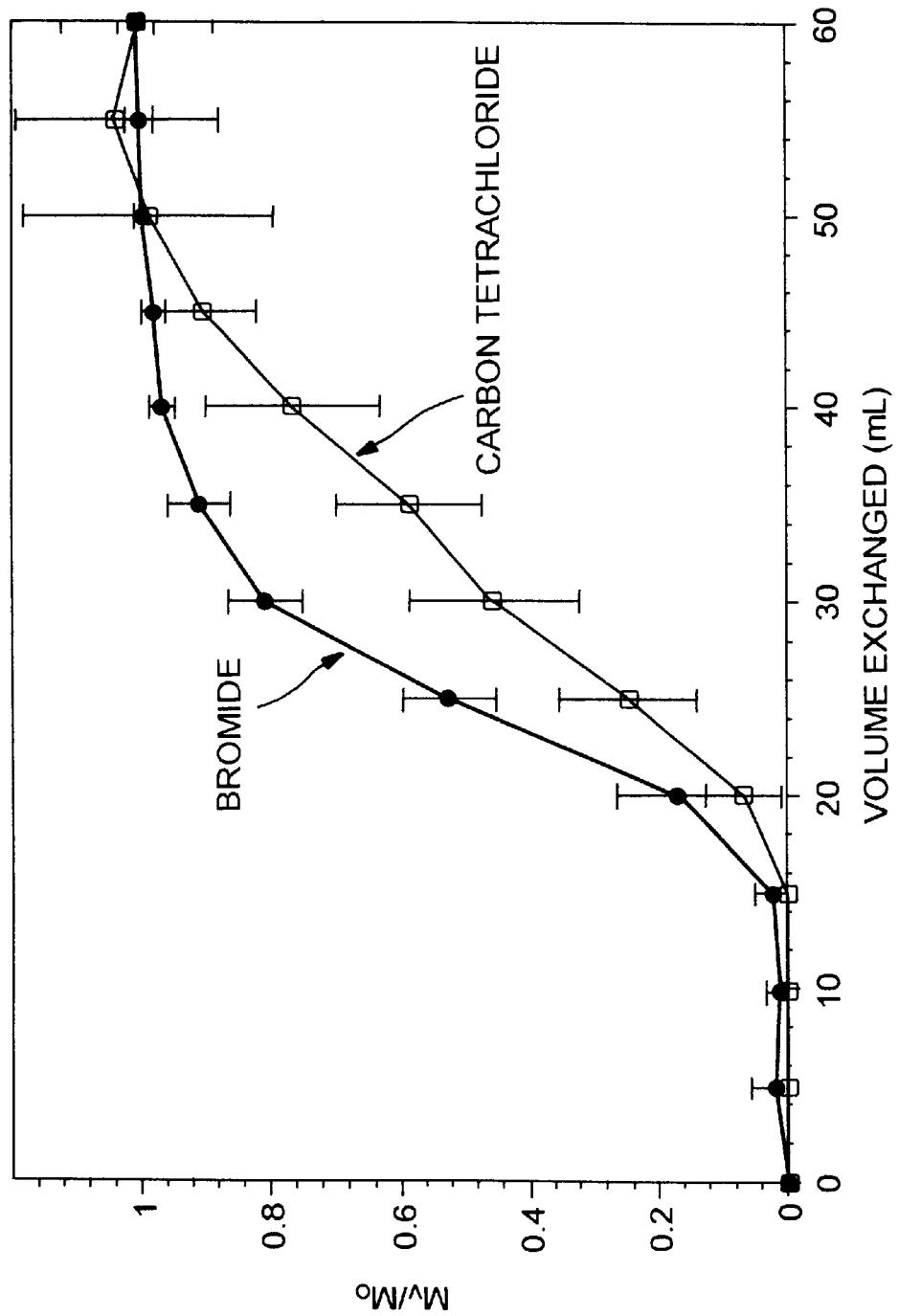
FIG. 16 shows breakthrough profile for bromide and CT composited from columns 1–9.

Composite breakthrough profiles were developed for CT and bromide for each of the three column sets (FIGS. 15A, 15B, 15C) and the complete set of nine columns (FIG. 16). As illustrated in the figures, CT was retarded in comparison to bromide. CT concentrations first were observed in the columns after 20 mL of pore fluids had been exchanged. Saturation of a column during an exchange event was achieved after exchange of 45–50 mL of CT groundwater. Concentrations within the first four and last five 5 mL fractions of fluids emerging from the columns during exchanges were averaged to determine $C_1$ and $C_2$, respectively. The CT breakthrough profile composited from the complete set of nine columns was typical of flow through a closed vessel (Froment, G. F. and K. B. Bischoff, Chemical Reactor Analysis and Design, 2nd Ed. John Wiley & Sons, pages 517–537(1990)) with a dispersion coefficient, $D_{dim}$, of less than 160 cm²/hr (Table 6).

The ratio of solute mass sorbed to aquifer solids to the mass of the solute in pore fluids defines the equilibrium partition coefficient, $R_p$. A summary of the change in the magnitude of $R_p$ for each column set is presented on FIG. 17. After 5 to 6 exchanges in each column set, $R_p$ values stabilized, indicating that sorption was essentially complete. The resulting "equilibrium" $R_p$ values range from a low of 0.3 (Column 9) to a high of about 1.3 (Column 1) (Table. 7). Therefore, retardation factors of 1.3 to 2.3 characterize the movement of CT relative to the rate of groundwater flow in the columns of repacked aquifer solids.

From the values of $R_p$ reported in Table 7, a range of distribution coefficients were calculated. Kd values between 0.1 cm³/g to 0.43 cm³/g were estimated (Table 7). This indicates that 33% to 70% of the total, CT mass in the columns was retained on the solid matrix following the completion of sorption. In general., the magnitude of sorption was most significant and comparable in column sets 1 and 2.

EXAMPLE 12

Transport of Strain PsKC and Colonization of Aquifer Materials

Figure 18:
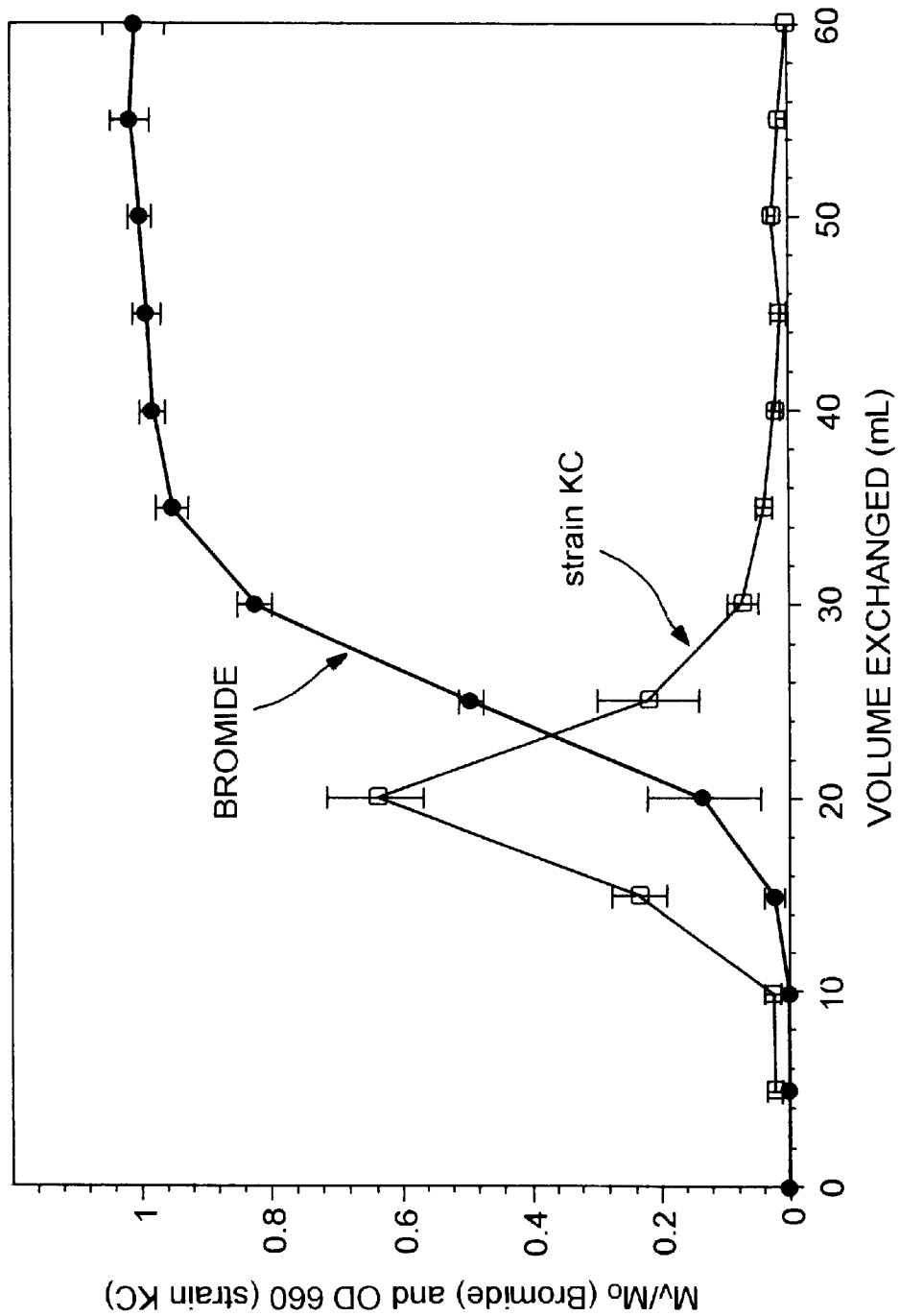
FIG. 18 shows breakthrough of strain PsKC in column set 1 (columns 1–3) as compared to the breakthrough of bromide for that column set.

As illustrated in FIG. 18, strain KC is, readily transported through re-packed Schoolcraft aquifer solids. In fact, breakthrough was more rapid than the average linear velocity of the exchange fluids (as defined by bromide breakthrough), probably owing to charge and/or pore size exclusion. Only about 40% of the mass of cells introduced were washed from the inoculated columns during the first exchange following inoculation. The remaining 60% were retained on the column. The mechanism of retention is unknown.

Figure 19:
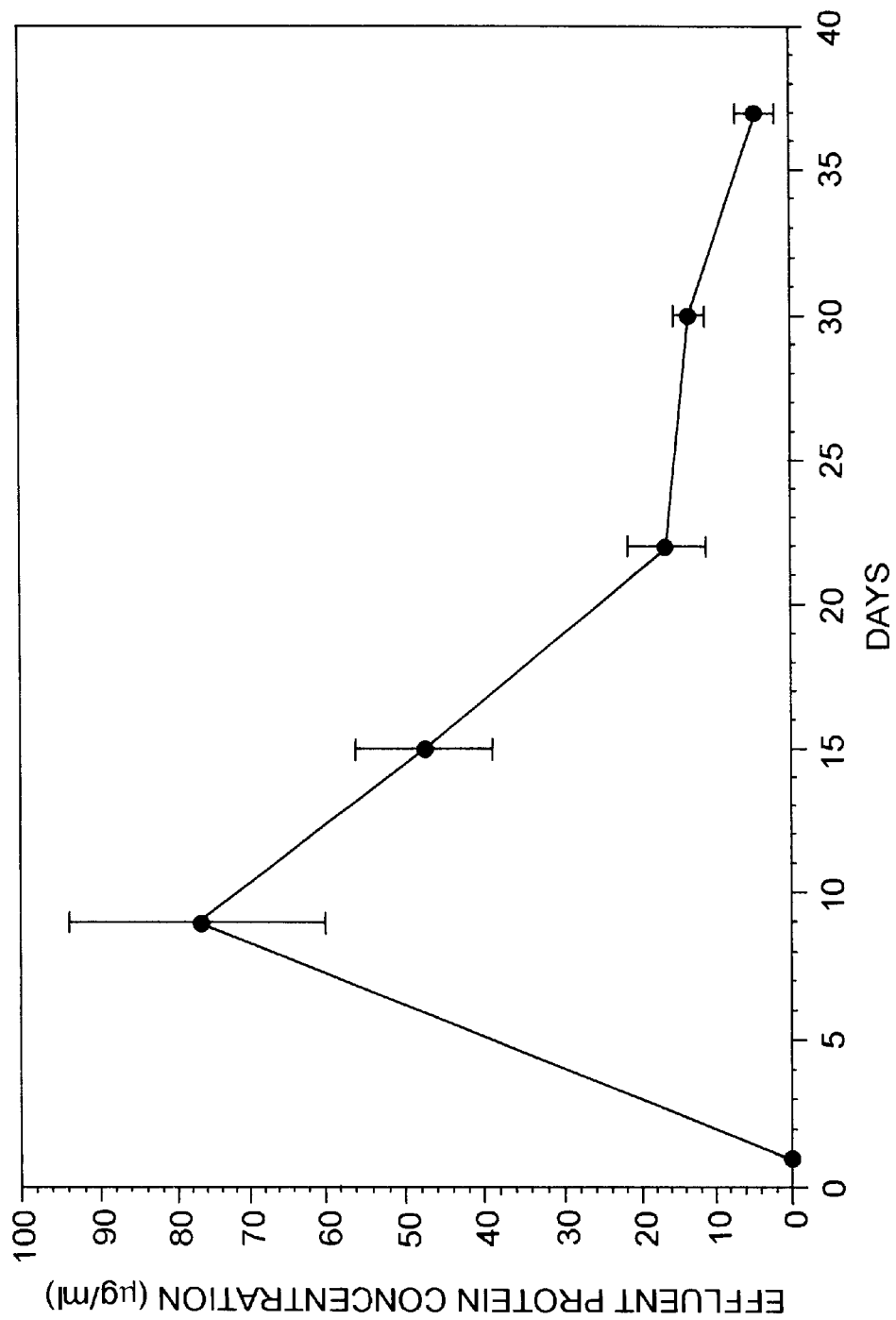
FIG. 19 shows effluent protein concentrations as measured in column set 1 (columns 1–3) during exchange events following inoculation.

FIG. 19 illustrates the incremental growth of strain PsKC as estimated from protein levels measured during each exchange following inoculation. Strain PsKC cells remaining in each column after inoculation (i.e. about $2.6 \times 10^{10}$ cells/mL) provided an ample inoculum for the aquifer materials. Growth occurred rapidly within the first 15 days following inoculation. Protein levels stabilized after 22 to 25 days, suggesting a balance between growth and decay. The results from standard plate counts and MPN analyses (data not shown) reveal that the overwhelming majority of suspended growth cell forming units (CFUs) in column set 1 exhibited a colony morphology distinctive of strain KC. No net accumulation of protein were observed in the effluent samples from either column set 2 or column set 3 following niche-adjustment.

EXAMPLE 13

Biotransformation of CT

Prior to niche adjustment, sorption was virtually complete in each of the three column sets, as evidenced by the lack of significant removal of CT between exchanges. After niche adjustment, CT removal resumed in the inoculated column set (columns 1–3), indicating biotransformation of CT.

Figure 20:
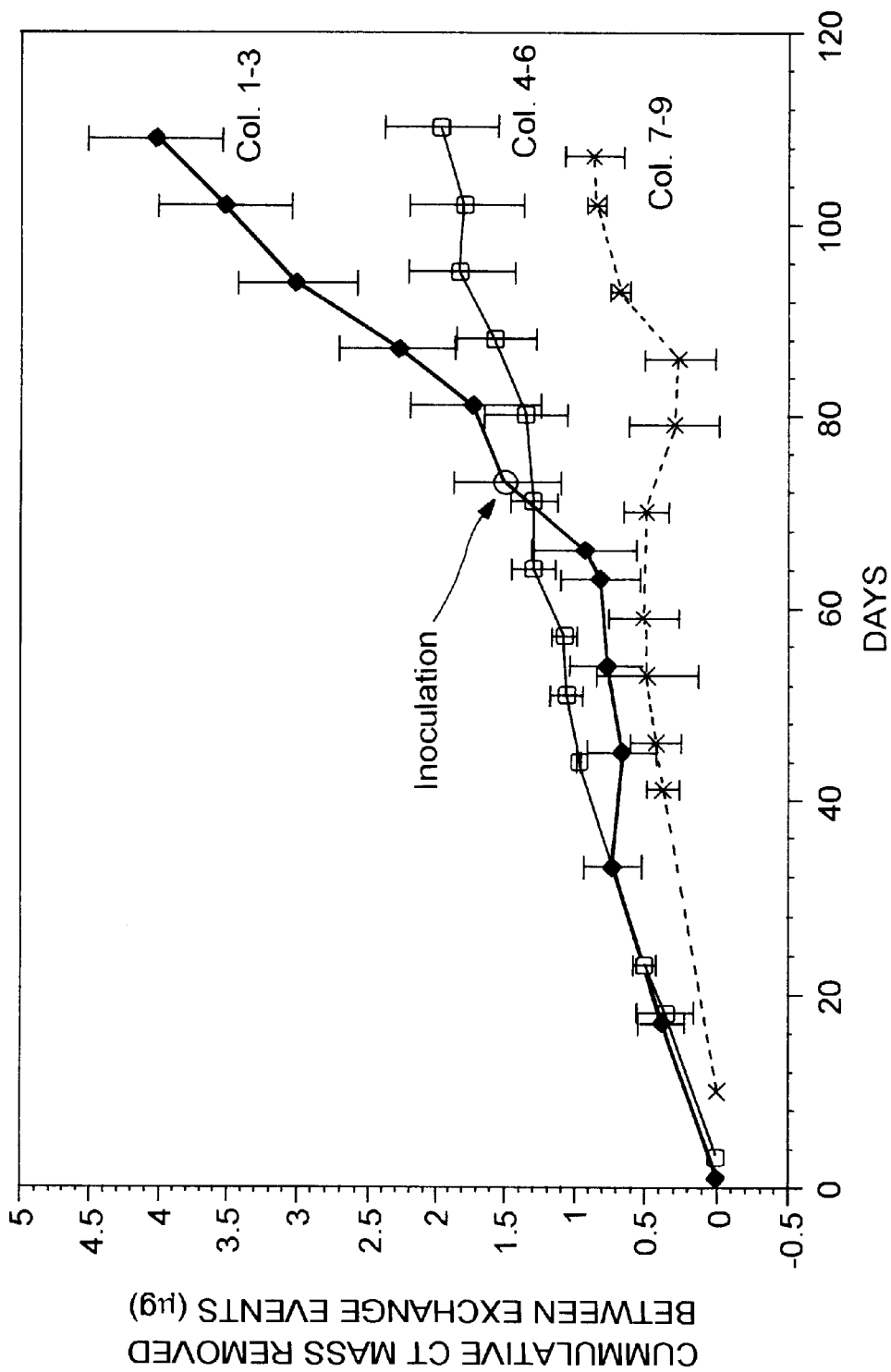
FIG. 20 shows CT mass removal measured over the duration of the experiment.

FIG. 20 illustrates the cumulative removal of CT within each of the three column sets over the duration of the study. CT removal increased sharply in column set 1 following inoculation with strain PsKC. No CF was detected in effluent samples from column set 1. No distinct increase in CT uptake was observed in the other two column sets. For column set 3, this observation was expected. However, there was some expectation that niche adjustment within the non-sterilized column set (column set 2) would result in stimulation of indigenous microorganisms capable of transforming CT. Although there was some evidence of limited CT removal in column set 2 following niche adjustment, the trend of CT uptake was neither distinct nor consistent.

FIG. 20 reveals a trend that was common to each of the three inoculated columns. After inoculation, CT levels steadily decreased. With the exception of the period prior to the last exchange event (which coincided with a sharp increase in mass loading), CT levels decreased at a relatively consistent rate. Further, CT removal during this period was equal to or exceeded the mass of CT loaded into the columns during an exchange, indicating removal of sorbed contaminant.

Figure 21:
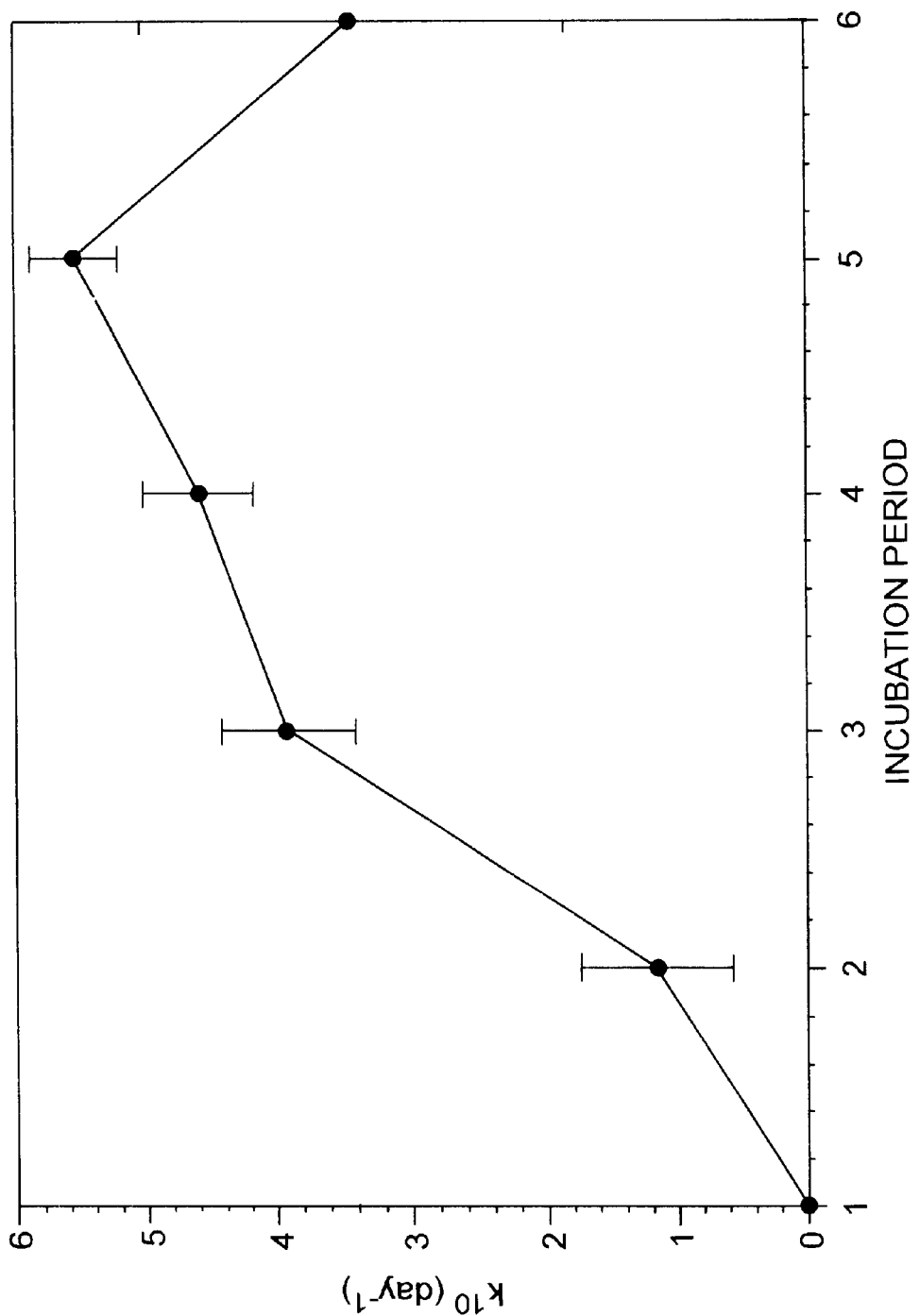
FIG. 21 shows apparent first order rate coefficient as measured in column set 1 (columns 1–3) during exchange events following inoculation.

FIG. 21 illustrates changes in the apparent first order rate of CT mass removal in column set 1 during the period of niche adjustment. From these data, an average first order rate constant (k") of 4.14 day$^{-1}$ was obtained. Laboratory studies have shown that the rate of CT transformation in batch experiments is a function of culture age, and decay of transformation activity occurs as cells enter a stationary phase (Tatara, G. M., et al., Applied and Environmental Microbiology, Vol. 59, No. 7, pp. 2126–2131 (1993)). The k" value reported herein does not correct for this loss of this activity. Approximately 50% to 70% of the mass of soluble CT input into column set 1 was removed during the incubation periods between exchanges.

The cumulative mass removal data from the column experiments indicate that strain KC will co-metabolize CT in niche-adjusted Schoolcraft aquifer materials. The apparent first order rate coefficient reported here, although slightly lower than anticipated, is high enough to expect that favorable rates of CT transformation will be attainable from engineered bioaugmentation of Plume A.

Repacking of the Schoolcraft aquifer solids resulted in a significant increase in effective porosity. Typical values of porosity for close-packed, medium grained, alluvial sands are 15–30% (Freeze, R. A. and J. A. Cherry, Groundwater, Prentice-Hall, Englewood Cliffs, 15–79 (1979)). Data collected during aquifer performance tests in the vicinity of Plume A revealed that specific yield values of 10–20% are typical of the Schoolcraft aquifer materials (Brown & Root Environmental). Ground water models developed during previous MDNR-sponsored investigations have assumed porosities of 20–25%. Thus, column packing may have resulted in a 50–100% increase in effective porosity. As a result of the increase in porosity from re-packing, the magnitude of CT sorption that was quantified was less than would be expected in the field. However, the distribution coefficients estimated from the sorption experiments were consistent with fitted values obtained by contaminant transport modeling efforts at the Schoolcraft site. Since the apparent first order rate coefficient reported herein was corrected for sorption, it is likely to be similar to the removal rate expected in the field.

The discrepancy between laboratory and field estimates of effective porosity must also be considered when evaluating the transport characteristics of strain PsKC. It is probable that strain KC will be transported somewhat less effectively under field conditions because of cell straining in materials of lower porosity.

Column experiments appear to be an effective means for evaluating the potential for bioaugmentation. The experimental protocols were simple, and results were produced in a time-frame typical of bench-scale treatability studies of soil and groundwater remediation technologies. In addition, the use of columns enabled simulation of the anticipated field-scale sequence of chemical additions and inoculation.

The results indicate that strain PsKC is readily transported through repacked Schoolcraft aquifer materials. After inoculation, strain PsKC rapidly grew and colonized the aquifer materials. The expression of CT transformation activity was immediate and significant. Up to 70% removal of soluble CT was observed over periods of approximately 7 to 9 days.

EXAMPLE 14

Kinetic growth parameters for Pseudomonas sp. strain KC and the indigenous Schoolcraft aquifer flora were obtained using Schoolcraft aquifer water. For determination of the Pseudomonas KC growth parameters, the Schoolcraft aquifer water was pasteurized overnight in a 65° incubator in sealed 500 ml Wheaton bottles. After cooling, 5g $NaHCO_3$/L was added as a buffer and to adjust the initial pH to approximately 8.2. Initial concentrations of acetate and nitrate were adjusted to approximately 30 and 12 mM, respectively. The Pseudomonas KC inocula consisted of a 1% 72 hour aerobic medium D grown starter culture that had been washed in pasteurized Schoolcraft aquifer water.

The Schoolcraft flora samples consisted of Schoolcraft aquifer water in 500 ml Wheaton bottles with $NaHCO_3$, acetate, and nitrate concentrations adjusted to initial values similar to that of the Pseudomonas KC samples.

TABLE 8

Growth Parameters for Pseudomonas sp. strain KC (P.KC) and Schoolcraft Flora (S) in Schoolcraft Aquifer Water.

| Kinetic Parameter | P.KC Avg. | P.KC St.Dev. | School. Avg. | School. St.Dev. |
|---|---|---|---|---|
| $\mu m$, max. specific growth rate (days$^{-1}$) (Optical Density @660 nm) | 2.68 | 0.97 | 1.13 | 0.66 |
| Y, Yield mg cells/mg $NO_3^-$ (dry wt.) | 0.35 | 0.05 | 0.07 | 0.03 |
| km, max specific rate of substrate util. (mg $NO_3^-$/mg cells*day) | 6.97 | 0.46 | 17.9 | 4.65 |

Methods of calculation: $\mu m$: (In (final optical density/initial optical density))/time elapsed. Optical density measurements were taken using a spectrophotometer. The measurements used for the calculation were those yielding the greatest slope when plotted versus time. Y: ((maximum dry weight of each sample)—(dry weight of control))/(initial nitrate concentration). Various volumes were filtered through 0.2 $\mu m$ filter membranes, dried, and weighed to determine the dry weight value in mg/L. Nitrate measurements were made using ion chromatography. km: (maximum rate of nitrate utilization)/((dry weight at approximate time of max. nitrate utilization)—(dry weight of control)). Nitrate measurements used were those yielding the greatest slope when plotted versus time. The method for dry weight and nitrate measurements was the same as for the yield calculation.

The result of this Example is that PsKC grows more rapidly and to a higher yield at pH 8.2, than the indigenous microorganisms.

Toxicology assessment was made on the CT transformation products utilizing Pimephales promelas (fathead minnow) acute and chronic exposure to 100% transformation effluent, exposure of two different human cell lines to 100% transformation effluent, exposure of corn (Zea mays) seeds and seedlings to 100% effluent and various cell concentrations, as well as MICROTOX and MUTATOX toxicity and mutagenicity screening tests. No evidence of toxicity was observed as shown in Table 9. The effluent was the Schoolcraft water.

TABLE 9

Toxicology Screening of Pseudomonas sp. Strain KC carbon tetrachloride transformation products

| Assay | Result |
|---|---|
| 1) Acute (96 hr) Fathead Minnow (Pimephales promelas) Survival Test | No evidence of toxicity (100% survival) |
| 2) Chronic (7 day) Fathead Minnow (Pimephales promelas) Survival Test | No evidence of toxicity (95% survival, 98.6% control growth |
| 3) MICROTOX[1] Assay | No evidence of toxicity at 90, 45, 22.5 or 11.25% effluent |
| 4) MUTATOX[2] Assay | No evidence of toxicity at 90, 45, 22.5 or 11.25% effluent |
| 5) Human Fibroblast Cell Exposure: SL 88 non-transformed cell | No evidence of toxicity |

TABLE 9-continued

Toxicology Screening of *Pseudomonas sp.*
Strain KC carbon tetrachloride transformation
products

| Assay | Result |
|---|---|
| line | (101–109% control survival) |
| HT 1080 chemically transformed cell line | No evidence of toxicity (125–143% control survival) |
| 6) Corn Germination in effluent | |
| Ferrey Morse strain 9000 | No evidence of toxicity (122% of control germination) |
| Ferrey Morse strain 9061 | No evidence of toxicity (136% of control germination) |
| 7) Corn Germination in soil inoculated with Pseudomonas KC | No evidence of toxicity |
| Pseudomonas KC cells/gram soil | % of control germination |
| $10^6$ | 100 |
| $10^7$ | 81 |
| $10^8$ | 110 |

[1]MICROTOX 500, Microbics Corporation, Carlsbad, CA.
[2]Microbics Corporation, Carlsbad, CA. These assays measure toxicity and mutagenicity of the transformation products.
The various plants, cell lines, and animals are available at Michigan State University, East Lansing, Michigan.

It is intended that the foregoing description be only illustrative of the present invention and that the present invention be limited only by the hereinafter appended claims.

We claim:

1. In a method of treating an environment of soil or water containing carbon tetrachloride (CT) and resident bacteria and having a neutral pH, the improvement which comprises:
   (a) adjusting the soil or water being treated to an alkaline pH which suppresses the resident bacteria in the soil or water;
   (b) providing cells of Pseudomonas PsKC deposited as ATCC 55595 and mutants thereof possessing the capability of PsKC for degradation of the CT which acts upon the CT at the alkaline pH in the soil or water while maintaining the alkaline pH of step (a) under anaerobic conditions and at a temperature so that the CT is converted to carbon dioxide and a non-volatile fraction end product, wherein the cells are grown in a culture medium containing a carbon source and a nitrogen source to a level prior to being provided in the soil or water, which cells are introduced to the soil or water to provide at least about $10^4$ CFU per gram of the soil or water and which cells convert the CT to carbon dioxide and the end product while the resident bacteria are suppressed; and
   (c) reversing the pH to a more neutral pH similar to the neutral pH of the soil or water before the pH adjustment of step (a).

2. The method of claim 1 wherein the alkaline pH of the soil or water is adjusted and in step (a) wherein after step (b) the alkaline pH of untreated soil or water, the soil or water is adjusted to the neutral pH of the soil or water before the treatment.

3. The method of claim 1 wherein the alkaline pH is between about 7.8 and 8.2.

4. The method of claim 1 wherein the soil or water is in the environment.

5. The method of claim 4 wherein an area in the environment containing the CT is adjusted to the alkaline pH in step (a) so as to limit colonization by the Pseudomonas PsKC to the area in step (b).

6. The method of claim 1 wherein the Pseudomonas PsKC is grown in a synthetic medium containing a carbon source and a nitrogen source and which is low in soluble iron salts to produce the cells which are provided in step (b).

7. The method of claim 1 wherein the soil or water is in the environment, wherein the Pseudomonas PsKC has been isolated and grown in a defined media containing a carbon source and a nitrogen source and which is low in soluble iron salts to produce the cells which are provided in step (b); wherein in step (b) the pH is between about 7.8 and 8.2 and wherein after step (b) the pH of the soil or water is adjusted to a more neutral pH similar to the neutral pH of the soil or water before the pH adjustment of step (a).

8. The method of claim 7 wherein an area in the environment containing the resident bacteria is adjusted to the alkaline pH which is between 7.8 and 8.2 in step (a).

9. The method of claim 8 wherein in step (b) the Pseudomonas PsKC is present in the soil or water at a level between about $10^5$ and $10^6$ CFU per gram.

10. The method of claim 1 wherein in step (b) the soil or water is amended with a carbon source and an electron acceptor for the Pseudomonas PsKC.

11. In a method of treating an environment of soil or water in situ contaminated with carbon tetrachloride and containing resident bacteria and having a neutral pH, the improvement which comprises:
   (a) adjusting the soil or water being treated to an alkaline pH between about 7.8 and 8.2 which suppresses resident bacteria;
   (b) providing a concentrate of cells of Pseudomonas PsKC deposited as ATCC 55595 and mutants thereof at a level of the cells of about $10^4$ CFU per gram possessing the capability of the Pseudomonas PsKC for degradation of the carbon tetrachloride in the soil or water, while maintaining the alkaline pH of step (a), under anaerobic conditions and at a temperature between about 5 and 30° C. so that the carbon tetrachloride is converted to carbon dioxide and a non-volatile fraction, wherein the cells are grown in a culture medium containing a carbon source and a nitrogen source to a level prior to being provided in the soil or water, which cells are introduced into the soil or water to provide at least about $10^4$ CFU per gram of the soil or water and which cells convert the CT to carbon dioxide and an end product while the resident bacteria are suppressed; and
   (c) adjusting the pH to a more neutral pH similar to the neutral pH of the soil or water before the pH adjustment of step (a).

12. The method of claim 11 wherein the Pseudomonas PsKC is grown in a synthetic medium containing a carbon source and a nitrogen source which medium is low in soluble iron salts to produce the cells which are provided in step (b).

13. The method of claim 11 wherein the soil is in the environment.

14. The method of claim 11 wherein in step (a) an area in the environment containing the carbon tetrachloride is adjusted to the alkaline pH.

15. The method of claim 11 wherein in step (b) the cells are provided in the soil or water at a level between about $10^5$ and $10^6$ CFU per gram.

16. The method of claim 11 wherein the soil or water is amended in step (b) with a carbon source and an electron acceptor for the Pseudomonas PsKC to enable the growth of the Pseudomonas PsKC.

* * * * *

UNITED STATES PATENT AND TRADEMARK OFFICE
CERTIFICATE OF CORRECTION

PATENT NO. : 6,613,558 B1
DATED : September 2, 2003
INVENTOR(S) : Michael J. Dybas, Craig S. Criddle and Gregory M. Tatara It is certified that error appears in the above-identified patent and that said Letters Patent is hereby corrected as shown below:

Column 5,
Line 65, "PSKC" should read -- PsKC --.

Column 6,
Line 65, "(PSKC)" should read -- (PsKC) --.

Column 8,
Line 18, after line 28 insert the heading -- Chemicals --.
Line 26, "$K_2HPO_{41}$" should be -- $K_2HPO_4$, --.
Line 34, "6H2O" should be -- $6H_2O$ --.
Line 34, "$H_3BO3$" should be -- $H_3BO_3$ --.
Line 54, "25mM PO4 3," should be -- 25mM $PO_4^{3-}$ --.
Line 55, "$NO_3$," should be -- $NO_3$- --.
Line 59, "(2)" should be inserted after "N.J.)," and before "a modified".

Column 14,
Line 23, "PSKC" should read -- PsKC --.
Line 34, "CT. organism" should be -- CT. Organism --.

Column 16,
Line 34, "(103-105 cfu/ml)" should be -- ($10^3$-$10^5$ cfu/ml) --.

Column 22,
Line 22, "$(C_2)_{i1}$" should be -- $(C_2)_{I-1}$ --.
Line 45, "$_tR$" should be -- $R_t$ --.

Column 24,
Table 7, line 3, Heading "Column Bet" should read -- Column Set --.
Table 7, table column 4, line 12, ".23" should read -- 23 --.

UNITED STATES PATENT AND TRADEMARK OFFICE
CERTIFICATE OF CORRECTION

PATENT NO.    : 6,613,558 B1
DATED         : September 2, 2003
INVENTOR(S)   : Michael J. Dybas, Craig S. Criddle and Gregory M. Tatara It is certified that error appears in the above-identified patent and that said Letters Patent is hereby corrected as shown below:

<u>Column 25,</u>
Line 61, "Kd" should be -- $K_d$ --.

Signed and Sealed this

Twenty-third Day of December, 2003

JAMES E. ROGAN
*Director of the United States Patent and Trademark Office*